(12) United States Patent
Ohori et al.

(10) Patent No.: US 11,547,743 B2
(45) Date of Patent: Jan. 10, 2023

(54) LYOPHILIZED FORMULATION OF HGF

(71) Applicant: EISAI R&D MANAGEMENT CO., LTD., Tokyo (JP)

(72) Inventors: Ryo Ohori, Gifu (JP); Kanta Horie, Gifu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/305,049

(22) PCT Filed: Apr. 24, 2015

(86) PCT No.: PCT/JP2015/062523
§ 371 (c)(1),
(2) Date: Oct. 18, 2016

(87) PCT Pub. No.: WO2015/166885
PCT Pub. Date: Nov. 5, 2015

(65) Prior Publication Data
US 2017/0189487 A1   Jul. 6, 2017

(30) Foreign Application Priority Data
Apr. 28, 2014   (JP) .............................. JP2014-092888

(51) Int. Cl.
| | |
|---|---|
| A61K 38/18 | (2006.01) |
| A61K 47/18 | (2017.01) |
| A61K 47/26 | (2006.01) |
| A61K 9/19 | (2006.01) |
| A61K 38/00 | (2006.01) |
| A61K 47/02 | (2006.01) |

(52) U.S. Cl.
CPC ............ *A61K 38/1833* (2013.01); *A61K 9/19* (2013.01); *A61K 38/00* (2013.01); *A61K 47/02* (2013.01); *A61K 47/18* (2013.01); *A61K 47/183* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 5,004,805 | A | 4/1991 | Gohda et al. |
| 5,466,593 | A | 11/1995 | Shimomura et al. |
| 5,587,359 | A | 12/1996 | Higashio et al. |
| 5,677,164 | A | 10/1997 | Shimomura et al. |
| 5,804,557 | A * | 9/1998 | Cleland ............... A61K 9/1694 424/85.7 |
| 7,741,096 | B2 | 6/2010 | Eigenbrot, Jr. et al. |
| 2001/0051604 | A1 | 12/2001 | Tanaka et al. |
| 2005/0220758 | A1 | 10/2005 | Zobel et al. |
| 2009/0233863 | A1 | 9/2009 | Adachi et al. |
| 2010/0137213 | A1 | 6/2010 | Fernandez et al. |
| 2013/0071931 | A1 | 3/2013 | Ishikawa |
| 2013/0142792 | A1 | 6/2013 | Rothlein et al. |
| 2014/0234341 | A1 | 8/2014 | Tsubouchi et al. |
| 2019/0000623 | A1 | 2/2019 | Shimizu et al. |
| 2020/0341014 | A1 | 10/2020 | Kimura et al. |

FOREIGN PATENT DOCUMENTS

| | | |
|---|---|---|
| CN | 1367703 A | 9/2002 |
| CN | 102271707 | 12/2011 |
| EP | 0596524 | 5/1994 |
| EP | 1180368 | 2/2002 |
| JP | S63-022526 | 1/1988 |
| JP | H03-285693 | 12/1991 |
| JP | H04-030000 | 1/1992 |
| JP | H05-103670 | 4/1993 |
| JP | H5-103670 A | 4/1993 |
| JP | H05-111383 | 5/1993 |
| JP | H06-153966 | 6/1994 |
| JP | H6-153966 A | 6/1994 |
| JP | 2577091 B | 1/1997 |
| JP | H09-025241 | 1/1997 |
| JP | 2747979 B | 5/1998 |
| JP | H10-167982 | 6/1998 |
| JP | 2859577 B | 2/1999 |
| JP | H11-056382 | 3/1999 |
| JP | 3072628 B | 7/2000 |
| JP | 3213985 B | 10/2001 |
| JP | 2002-356500 A | 12/2002 |

(Continued)

OTHER PUBLICATIONS

Sino Biological Human HGF Catalog No. 10463-HNAS product data sheet with Material Safety Data Sheet, Jun. 8, 2012, downloaded Jun. 22, 2017 from http://www.sinobiological.com/HGF-Protein-g-5402.html.*
Sino Biological Mouse HGF Catalog No. 50038-MNAH product data sheet with Material Safety Data Sheet, Jun. 8, 2012, downloaded Jun. 22, 2017 from http://www.sinobiological.com/HGF-Hepatocyte-Growth-Factor-g-10551.html.*
Suzuki, Y. "Production Technology and Quality Problems of Freeze-Dried Parenteral Formulations", Pharm. Tech. Japan, vol. 8, No. 1, p. 75-87, 1992 (with English Translation).
Office Action issued in Pakistan Patent Application No. 234/2015, dated Oct. 6, 2017, 2 pages (English translation).
Office Action issued in Israeli Patent Application No. 248377, dated Jan. 15, 2018, 5 pages (with English translation).
Response to Office Action filed in Pakistani Patent Application No. 234/2015, dated Jan. 11, 2018, 7 pages.

(Continued)

*Primary Examiner* — Marianne P Allen
(74) *Attorney, Agent, or Firm* — Fish & Richardson P.C.

(57) ABSTRACT

An object of the present invention is to provide a lyophilized formulation having improved storage stability of hepatic growth factor compared to conventional lyophilized formulations. The present invention provides a lyophilized formulation comprising (1) a hepatic growth factor, (2) trehalose and (3) one or more compounds selected from the group consisting of arginine, histidine, lysine, meglumine, glutamic acid, aspartic acid, proline, creatine, creatinine, tris (hydroxymethyl)aminomethane, and pharmaceutically acceptable salts thereof.

4 Claims, 3 Drawing Sheets
Specification includes a Sequence Listing.

(56) References Cited

FOREIGN PATENT DOCUMENTS

| JP | 2010-513462 | | 4/2010 |
|---|---|---|---|
| JP | 2012-051822 | | 3/2012 |
| JP | 2012-507553 | | 3/2012 |
| JP | 2013-520166 | | 6/2013 |
| KR | 10-2002-0064141 | | 8/2002 |
| RU | 2113480 | C | 6/1998 |
| RU | 2316348 | | 2/2008 |
| RU | 2506946 | C | 2/2014 |
| TW | 201141507 | A | 12/2011 |
| WO | 1990/010651 | | 9/1990 |
| WO | 2000/072873 | | 12/2000 |
| WO | WO 2006/014928 | | 2/2006 |
| WO | WO 2007/122975 | | 11/2007 |
| WO | 2008/078189 | | 7/2008 |
| WO | 2008/102849 | | 8/2008 |
| WO | WO 2011/049868 | | 4/2011 |
| WO | WO 2012/144535 | | 10/2012 |
| WO | WO 2014/063128 | | 4/2014 |

OTHER PUBLICATIONS

Response filed on May 11, 2018 for the Israeli Patent Application No. 248377.
Response file on Jul. 4, 2018 for the European Patent Application No. 15786509.8.
Supplementary European Search Report issued in European Application No. 15786509.8 dated Jan. 3, 2018, 6 pages.
International Preliminary Report on Patentability in International Application No. PCT/JP2015/062523, dated Nov. 1, 2016, 4 pages.
Response and Amendment for Pakistani Patent Application No. 234-2015, filed on Nov. 27, 2018, 4 pages.
Written Opinion in International Application No. PCT/JP2015/062523, dated Jul. 28, 2015, 4 pages (English translation).
Office Action in Pakistani Patent Application No. 234/2015, dated Oct. 4, 2018, 2 pages.
Chapanian R.et al., "Combined and sequential delivery of bioactive VEGF165 and HGF from poly(trimethylene carbonate) based photo-crosslinked elastomers," Journal of Controlled Release, 2010, vol. 143, p. 53-63.
Nakamura et al., "Molecular cloning and expression of human hepatocyte growth factor", Nature, 1989, vol. 342, p. 440-443.
Rafferty et al., "International Standards for hepatocyte growth factor/scatter factor; initial assessment of candidate materials and their evaluation by multicentre collaborative study", Journal of Immunological Methods, vol. 258, p. 1-11, 2001.
The Japanese Pharmacopoeia Sixteenth Edition, p. 113-116, 973-974 (Mar. 24, 2011) with English translation.
Notice of Allowance in Taiwanese Patent Application No. 104113328, dated Jun. 13, 2019, 5 pages (with English Translation).
Office Action in Australian Patent Application No. 2015254307, dated Jun. 25, 2019, 3 pages.
Amendment and Response to Japanese Office Action in Japanese Patent Application No. 2016-516354, dated Feb. 7, 2019, 11 pages (with English Translation).
Arshinova et al., "Excipients in technology of lyophilization of drug preparations," Scientific and Manufacturing Journal—Development and Registration of Medicaments, 2013, pp. 20-25 (with English Translation).
Office Action in Israeli Patent Application No. 248377, dated Nov. 12, 2018, 6 pages (with English Translation).
Office Action in Japanese Patent Application No. 2016-516354, dated Dec. 11, 2018, 6 pages (with English Translation).
Office Action in Russian Patent Application No. 2016146121, dated Nov. 28, 2018, 12 pages (with English Translation).
Office Action in Taiwanese Patent Application No. 104113328, dated Jan. 9, 2019, 7 pages (with English Translation).
Response to Office Action in Israeli Patent Application No. 248377, dated Feb. 26, 2019, 6 pages (with English Translation).
Search Report in Russian Patent Application No. 2016146121, dated Nov. 26, 2018, 6 pages (with English Translation).
Gohda et al., "Purification and partial characterization of hepatocyte growth factor from plasma of a patient with fulminant hepatic failure," The Journal of Clinical Investigation, (1988), 81(2):414-419.
International Search Report in International Application No. PCT/JP2017/010355, dated May 30, 2017, 4 pages. (with English Translation).
International Search Report in International Application No. PCT/JP2017/010587, dated May 23, 2017, 4 pages (with English Translation).
Kaibori et al., "Hepatocyte Growth Factor Stimulates Synthesis of Lipids and Secretion of Lipoproteins in Rat Hepatocytes," Hepatology, (1998), 27(5)1354-1361.
Kirchhofer et al., "Tissue Expression, Protease Specificity, and Kunitz Domain Functions of Hepatocyte Growth Factor Activator Inhibitor-1B (HAI-1B), a New Splice Variant of HAI-1," The Journal of Biological Chemistry, Jun. 18, 2003, 278(38):36341-36349.
Kosone et al., "HGF ameliorates a high-fat diet-induced fatty liver," American Journal of Physiology-Gastrointestinal and Liver Physiology, (2007), 293(1):G204-G210.
Nakamura et al., "Hepatocyte growth factor twenty years on: Much more than a growth factor," Journal of Gastroenterology and Hepatology, (2011), 26(S1):188-202.
Ota et al., "Changes in Blood Concentration of Human Hepatocyte Growth Factor (hHGF) and Apolipoprotein A-IV After Transcatheter Arterial Embolization (TAE) in Hepatocyte Cancer Patients," The Japanese Journal of Clinical and Experimental Medicine, (1994), 71(8):245-247 (with English Translation).
Stan et al., "Apo A-IV: an update on regulation and physiologic functions," Biochimica et Biophysica Acta, (2003), 1631(2):177-187.
Tahara et al., "Hepatocyte growth factor leads to recovery from alcohol-induced fatty liver in rats," The Journal of Clinical Investigation, (1999), 103(3):313-320.
Xu et al., "Transcriptional regulation of apolipoprotein A-IV by the transcription factor CREBH," Journal of Lipid Research, (2014), 55:850-859.
Xu et al., "Transforming growth factor-beta down-regulates apolipoprotein M in HepG2 cells," Biochimica et Biophysica Acta, (2004), 1683(1-3):33-37.
Office Action and Search Report in Chinese Patent Application No. 201580021294.9, dated Mar. 27, 2019, 12 pages (with English Translation).
Response and Amendment filed in Russian Patent Application No. 2016146121, dated Apr. 17, 2019, 8 pages (with English Translation).
Response filed in Taiwanese Patent Application No. 104113328, dated Mar. 25, 2019, 13 pages (with English Translation).
Amendment and Response filed in Russian Patent Application No. 2016146121, dated Apr. 9, 2019, 11 pages (with English Translation).
Amendment filed in Japanese Patent Application No. 2016-516354, dated Feb. 7, 2019, 3 pages (with English Translation).
Decision of Grant for Russian Patent Application No. 2016146121, dated Apr. 25, 2019, 12 pages, (with English Translation).
Decision of Grant for Japanese Patent Application No. 2016-516354, dated Jul. 24, 2019, 4 pages (with English Translation).
Notice of Allowance in Chinese Patent Application No. 201580021294.9, dated Sep. 19, 2019, 3 pages (with English Translation).
Office Action in Australian Patent Application No. 2015254307, dated Oct. 10, 2019, 3 pages.
Response and Amendment filed in Australian Patent Application No. 2015254307, dated Oct. 10, 2019, 10 pages.
Response filed in Australian Patent Application No. 2015254307, dated Oct. 14, 2019, 4 pages.
Response filed in Chinese Patent Application No. 201580021294.9, dated Aug. 7, 2019, 16 pages (with English Translation).
Telephonic Notice Response filed in Chinese Patent Application No. 201580021294.9, dated Aug. 26, 2019, 12 pages (with English Translation).

(56) References Cited

OTHER PUBLICATIONS

Office Action in Israeli Patent Application No. 261066, dated May 5, 2019, 6 pages (with English Translation).
Response and Amendment filed in Israeli Patent Application No. 261066, dated Aug. 21, 2019, 5 pages (with English Translation).
Supplemental Response and Amendment filed in Israeli Patent Application No. 261066, dated Sep. 3, 2019, 5 pages (with English Translation).
Cell Signaling Technology [Online], "ApoA4 (1D6B6) Mouse mAb," Feb. 2016, [Retrieved on Sep. 10, 2019], retrieved from: URL<https://media.cellsignal.com/pdf/5700.pdf>, 1 page.
European Extended Search Report in European Patent Application No. 17766767.2, dated Sep. 19, 2019, 7 pages.
Response and Amended Claims filed in European Patent Application No. 17766767.2, dated Nov. 19, 2019, 5 pages.
European Extended Search Report in European Patent Application No. 17766718.5, dated Oct. 22, 2019, 5 pages.
Office Action in U.S. Appl. No. 16/078,568, dated Oct. 28, 2019, 13 pages.
Response and Amendment filed in European Patent Application No. 17766718.5, dated Nov. 22, 2019, 9 pages.
Response filed in U.S. Appl. No. 16/078,568, dated Dec. 2, 2019, 7 pages.
Notice of Acceptance in Australian Patent Application No. 2015254307, dated Oct. 24, 2019, 3 pages.
Office Action in Indian Patent Application No. 201647036821, dated Nov. 27, 2019, 6 pages.
Office Action in Mexican Patent Application No. MX/a/2016/013667, dated Nov. 5, 2019, 8 pages (with English Translation).
Response filed in Mexican Patent Application No. MX/a/2016/013667, dated Jan. 8, 2020, 10 pages (with English Translation).
Notice of Allowance in Israeli Patent Application No. 248377, dated Jan. 15, 2020, 8 pages (with English Translation).
Notice of Allowance in Mexican Patent Application No. MX/a/2016/013667, dated Feb. 4, 2020, 5 pages (with English Translation).
Notice of Allowance in U.S. Appl. No. 16/078,568, dated Dec. 16, 2019, 13 pages.
Office Action in U.S. Appl. No. 16/078,568, dated Jun. 19, 2019, 10 pages.
Request for Continued Examination filed in U.S. Appl. No. 16/078,568, dated Mar. 13, 2020, 7 pages.
Request for Examination with the Voluntary Amendment in Singaporean Patent Application No. 10201809228R, filed Apr. 2, 2020, 10 pages.
Response filed in Indian Patent Application No. 201647036821, dated Apr. 14, 2020, 10 pages.
Response filed in U.S. Appl. No. 16/078,568, dated Sep. 9, 2019, 10 pages.
Acceptance Fee Receipt in Australian Patent Application No. 2015254307, dated Dec. 9, 2019, 1 page.
Certificate of Patent in Australian Patent No. 2015254307, granted on Feb. 20, 2020, 1 page.
Certificate of Patent in Japanese Patent No. 6568846, granted on Aug. 9, 2019, 2 pages (with English Translation).
Certificate of Patent in Russian Patent No. 2693472, granted on Jul. 3, 2019, 66 pages (with English Translation).
Certificate of Patent in Taiwanese Patent No. 1674902, granted on Oct. 21, 2019, 2 pages (with English Translation).
Official Receipt Payment of Request for Examination in Australian Patent Application No. 2015254307, dated Mar. 5, 2019, 1 page.
Official Receipt Payment of Request for Examination in Brazilian Patent Application No. BR112016025051-6, dated Mar. 7, 2018, 4 pages (with English Translation).
Request for Examination, Form 18, in Indian Patent Application No. 201647036821, dated Feb. 23, 2018, 1 page.
Request for Examination in Canadian Patent Application No. 2947396, dated Feb. 6, 2020, 1 page.

Request for Examination in Chinese Patent Application No. 201580021294.9, filed Oct. 26, 2016, 2 pages (with English Translation).
Request for Examination in Japanese Patent Application No. 2016-516354, filed Feb. 29, 2018, 2 pages (with English Translation).
Request for Examination in Korean Patent Application No. 10-2016-7029770, filed Nov. 18, 2019, 2 pages (with English Translation).
Request for Examination in Russian Patent Application No. 2016146121, dated Apr. 13, 2018, 2 pages (with English Translation).
Request for Examination in Taiwanese Patent Application No. 104113328. dated Mar. 8, 2018, 6 pages (with English Translation).
Technical Report in Brazilian Patent Application No. 112016025051-6, dated Mar. 5, 2020, 2 pages (with English Translation).
Communication pursuant to Article 94(3) EPC in European Patent Application No. 17766767.2, dated Jun. 23, 2020, 6 pages.
Notice of Allowance in U.S. Appl. No. 16/078,568, dated May 18, 2020, 12 pages.
Response filed in European Patent Application No. 17766767.2, dated Aug. 5, 2020, 7 pages.
Certificate of Patent for Israeli Patent No. 248377, granted on Jul. 31, 2020, 2 pages.
Office Action in U.S. Appl. No. 16/078,568, dated Sep. 9, 2020, 10 pages.
Preliminary Office Action with Technical Report in Brazilian Patent Application No. BR112016025051-6, dated Jun. 16, 2020, 8 pages (with English Translation).
Response and Amendment filed in Israeli Patent Application No. 261066, dated Aug. 27, 2020, 6 pages.
Shimomura et al., "A novel protease obtained from FBS-containing culture supernatant, that processes single chain form hepatocyte growth factor to two chain form in semm-free culture," Cytotechnology, 1992, 8(3):219-229.
Response to Restriction Requirement filed in U.S. Appl. No. 16/078,557, filed Sep. 28, 2020, 3 pages.
Restriction Requirement in U.S. Appl. No. 16/078,557, dated Aug. 26, 2020, 8 pages.
Apalikova et al., "Sorbing Polymers Based on Iron Oxyhydrates," Bulletin of Chelyabinsk Scientific Center, South Ural State University, Chelyabinsk, Russia, Aug. 2000, vol. 3, UDC:546.723-36 (with English Translation).
Office Action in Pakistani Patent Application No. 234/2015, dated Jan. 18, 2021, 2 pages.
Office Action in Russian Patent Application No. 2018130530, dated Dec. 16, 2020, 6 pages (with English Translation).
Response and Claim Amendment filed in Russian Patent Application No. 2018130530, dated Feb. 8, 2021, 6 pages (with English Translation).
Hüpeden et al., "Relative abundance of *Nitrotoga* spp. in a biofilter of a cold-freshwater aquaculture plant appears to be stimulated by slightly acidic pH," Applied and Environmental Microbiology, Mar. 2016, 82(6):1838-1845.
Kamimoto et al., "Hepatocyte growth factor prevents multiple organ injuries in endotoxemic mice through a heme oxygenase-1-dependent mechanism," Biochemical and Biophysical Research Communications, 2009, 380:333-337.
Mukai et al., "Activation of hepatocyte growth factor activator zymogen (pro-HGFA) by human kallikrein 1-related peptidases," The FEBS Journal, 2008, 275:1003-1017.
Notice of Allowance in U.S. Appl. No. 16/078,568, dated Dec. 22, 2020, 12 pages.
Office Action in Canadian Patent Application No. 2947396, dated Dec. 23, 2020, 4 pages.
Office Action in Israeli Patent Application No. 261066, dated Jul. 30, 2020, 6 pages (with English Translation).
Office Action in Japanese Patent Application No. 2018-505994, dated Aug. 3, 2020, 8 pages (with English Translation).
Office Action in Japanese Patent Application No. 2018-505994, dated Oct. 5, 2020, 6 pages (with English Translation).
Office Action in Japanese Patent Application No. 2018-505972, dated Sep. 23, 2020, 10 pages (with English Translation).
Office Action in Russian Patent Application No. 2018130530, dated Aug. 13, 2020, 16 pages (with English Translation).

(56) References Cited

OTHER PUBLICATIONS

Office Action in U.S. Appl. No. 16/078,557, dated Nov. 17, 2020, 37 pages.
Parr et al., "Expression of hepatocyte growth factor/scatter factor, its activator, inhibitors and the c-Met receptor in human cancer cells," International Journal of Oncology, Oct. 200, 19:857-863.
Response and Claim Amendment filed in Russian Patent Application No. 2018130530, dated Nov. 12, 2020, 10 pages (with English Translation).
Response filed in U.S. Appl. No. 16/078,568, dated Dec. 8, 2020, 8 pages.
Response to the Preliminary Office Action in Brazilian Patent Application No. BR112016025051-6, dated Sep. 8, 2020, to the Preliminary Office Action dated Jun. 16, 2020, 24 pages (with English Translation).
Selvarasu et al., "Combined In Silico Modeling and Metabolomics Analysis to Characterize Fed-Batch CHO Cell Culture," Biotechnology and Bioengineering, Jun. 2012, 109(6): 1415-1429.
Suzuki et al., "Skeletal Muscle Injury Induces Hepatocyte Growth Factor Expression in Spleen," Biochemical and Biophysical Research Communications, 2002, 292:709-714.
Written Argument and Amendment Response in Japanese Patent Application No. 2018-505994, dated Aug. 25, 2020, 11 pages (with English Translation).
Written Argument and Amendment Response in Japanese Patent Application No. 2018-505994, dated Oct. 26, 2020, 6 pages (with English Translation).
Written Argument and Amendment Response in Japanese Patent Application No. 2018-505972, dated Oct. 26, 2020, 9 pages (with English Translation).
Communication under Rule 71(3) EPC in European Patent Application No. 15786509.8, dated Feb. 16, 2021, 69 pages.
Kataoka et al., "Hepatocyte growth factor activator (HGFA): pathophysiological functions in vivo," MINIREVIEW, The FEBS Journal, 2010, 277(10):2230-2237.
Office Action in Indian Patent Application No. 201847031049, dated Oct. 19, 2020, 6 pages.
Office Action in Korean Patent Application No. 10-2018-7024470, dated Dec. 21, 2020, 5 pages (with English Translation).
Response filed in Indian Patent Application No. 201847031049, dated Feb. 15, 2021, 8 pages.
Response filed in Korean Patent Application No. 10-2018-7024470, dated Feb. 9, 2021, 19 pages (with English Translation).
Response filed in U.S. Appl. No. 16/078,557, dated Feb. 17, 2021, 9 pages.
Notice of Allowance in Japanese Patent Application No. 2018-505972, dated Mar. 22, 2021, 6 pages (with English Translation).
Office Action in Korean Patent Application No. 10-2016-7029770, dated Feb. 26, 2021, 7 pages (with English Translation).
IN Official Communication of the Intimation of Grant and Patent Certificate of Indian Patent No. 371199 in Indian Appln. No. 201647036821, dated Jul. 6, 2021, 2 pages (with English Translation).
Request for Continued Examination filed in U.S. Appl. No. 16/078,568, dated May 20, 2021, 5 pages.
Communication under Rule 71(3) EPC in European Patent Application No. 17766718.5, dated Apr. 28, 2021, 51 pages.
Decision of Grant for Russian Patent Application No. 2018130530, dated Apr. 7, 2021, 14 pages (with English Translation).
Letter Patent granted in Mexican Patent No. 372156, dated Mar. 11, 2021, 106 pages (with English Translation).
Notice of Allowance in Taiwanese Patent Application No. 108125333, dated Mar. 11, 2021, 7 pages (with English Translation).
Notice of Allowance in U.S. Appl. No. 16/078,568, dated Apr. 30, 2021, 8 pages.
Office Action in U.S. Appl. No. 16/078,557, dated May 12, 2021, 10 pages.
Office Action in U.S. Appl. No. 16/078,568, dated Mar. 22, 2021, 5 pages.
Request for Continued Examination filed in U.S. Appl. No. 16/078,568, dated Mar. 2, 2021, 5 pages.
Response and Amendment filed in Korean Patent Application No. 10-2016-7029770, dated Apr. 22, 2021, 17 pages (with English Translation).
Response filed in Canadian Patent Application No. 2,947,396, dated Apr. 8, 2021, 8 pages.
Response filed in U.S. Appl. No. 16/078,568, dated Apr. 9, 2021, 5 pages.
Voluntary Amendment filed in Taiwanese Patent Application No. 108125333, dated Jan. 15, 2020, 14 pages (with English Translation).
Communication pursuant to Article 94(3) EPC in European Patent Application No. 17766767.2, dated Apr. 6, 2021, 5 pages.
Letter Patent granted in Korean Patent No. 10-2291913, dated Aug. 13, 2021, 3 pages (with English Translation).
Office Action and Search Report in Chinese Patent Application No. 201780013057.7, dated Aug. 10, 2021, 15 pages (with English Translation).
Request for Continued Examination filed in U.S. Appl. No. 16/078,568, dated Aug. 25, 2021. 5 pages.
Response and Amendment filed in European Patent Application No. 17766767.2, dated Jul. 19, 2021, 19 pages.
Letter Patent granted in European Patent No. 3138575, dated Jul. 14, 2021, 2 pages.
Letter Patent granted in Taiwanese Patent No. 1728409, dated May 21, 2021, 2 pages (with English Translation).
Notice of Allowance in Canadian Patent Application No. 2947396, dated Jul. 23, 2021, 1 page (with English Translation).
Notice of Allowance in Israeli Patent Application No. 261066, dated Jun. 7, 2021, 7 pages (with English Translation).
Notice of Allowance in Korean Patent Application No. 10-2016-7029770, dated Jul. 28, 2021, 3 pages (with English Translation).
Notice of Allowance in U.S. Appl. No. 16/078,568, dated Jul. 27, 2021, 12 pages.
Request for Examination in Russian Patent Application No. 2019119586, dated Jul. 29, 2021, 2 pages (with English Translation).
Notice of Eligibility for Grant and Supplementary Examination Report in Singaporean Patent Application No. 10201809228R, dated Sep. 7, 2021, 4 pages.
Certificate of Patent and Notification of Grant in Singaporean Patent Application No. 10201809228R, dated Oct. 8, 2021, 3 pages.
Letter Patent granted in Canadian Patent No. 2947396, dated Oct. 19, 2021, 61 pages.
Response and Claim Amendment filed in Chinese Patent Application No. 201780013057.7, dated Oct. 26, 2021, 10 pages (English Translation only).
Certificate of Patent in Chinese Patent No. ZL 2017800130577, announced on Jan. 11, 2022, 4 pages (with English Translation).
Certificate of Patent in Israeli Patent No. 261066, granted on Dec. 1, 2022, 2 pages (with English Translation).
Notice of Eligibility for Grant and Support Therefor in Singaporean Patent Application No. 11201806843U, dated Jan. 12, 2022, 4 pages.
Notice to Grant a Patent for Invention in Chinese Patent Application No. 201780013057.7, dated Dec. 17, 2021, 2 pages (with English Translation).
Notification of Patent Registration in Chinese Patent Application No. 201780013057.7, dated Dec. 17, 2021, 2 pages (with English Translation).
Office Action in Russian Patent Application No. 2019119586, dated Jan. 25, 2022, 9 pages (with English Translation).
Search Report in Russian Patent Application No. 2019119586, dated Jan. 24, 2022, 4 pages (with English Translation).
Office Action in Australian Patent Application No. 2017232582, dated May 30, 2022, 3 pages.
Response filed in Australian Patent Application No. 2017232582, dated Jun. 20, 2022, 17 pages.
Certificate of Patent in Singaporean Patent No. 1120186843U, granted on Apr. 13, 2022, 1 page.
Notification of Grant in Singaporean Patent Application No. 11201806843U, dated Apr. 13, 2022, 2 pages.

(56) References Cited

OTHER PUBLICATIONS

Response filed in Russian Patent Application No. 2019119586, dated Apr. 29, 2022, 9 pages (with English Translation).
Decision of Grant for Russian Patent Application No. 2019119586, dated Jun. 25, 2022, 15 pages (with English Translation).
Office Action in Mexican Patent Application No. MX/a/2018/010283, dated May 24, 2022, 8 pages (with English Translation).
Response filed in Mexican Patent Application No. MX/a/2018/010283, dated Jul. 1, 2022, 17 pages (with English Translation).
Letter Patent granted in Australian Patent Application No. 2017232582, dated Oct. 27, 2022, 1 page.
Letter Patent granted in Russian Patent Application No. 2776108, dated Jul. 13, 2022, 5 pages, (with Cover Page Translation).
Letter Patent granted in Mexican Patent Application No. 395311, dated Sep. 5, 2022, 60 pages, (with Cover Page Translation).

* cited by examiner

SEQUENCE LISTING

<160> NUMBER OF SEQ ID NOS: 1

<210> SEQ ID NO 1
<211> LENGTH: 728
<212> TYPE: PRT
<213> ORGANISM: Human

<400> SEQUENCE: 1

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

```
Thr Leu Ile Lys Ile Asp Pro Ala Leu Lys Ile Lys Thr Lys Val
     50                  55                  60

Asn Thr Ala Asp Gln Cys Ala Asn Arg Cys Thr Arg Asn Lys Gly Leu
 65              70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
450                 455                 460
```

```
Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725
```

LYOPHILIZED FORMULATION OF HGF

SEQUENCE LISTING

This application contains a Sequence Listing that has been submitted electronically as an ASCII text file named SEQLIST.txt. The ASCII text file, created on Apr. 23, 2015, is 6,555 bytes in size. The material in the ASCII text file is hereby incorporated by reference in its entirety.

TECHNICAL FIELD

The present invention relates to a lyophilized formulation comprising hepatic growth factor.

SEQUENCE LISTING

This application contains a Sequence Listing that has been submitted electronically as an ASCII text file named SEQLIST.txt. The ASCII text file, created on Apr. 23, 2015, is 6,555 bytes in size. The material in the ASCII text file is hereby incorporated by reference in its entirety.

BACKGROUND

Hepatic growth factor (HGF) is a bioactive peptide having proliferation activity of hepatic parenchymal cells and has been found in various animal species. In humans, human hepatic growth factor (hHGF) has been found in plasma from patients with fulminant hepatitis (Patent Literature 1), and in recent years, recombinant human hepatic growth factor (rhHGF) can be mass-produced by biotechnology (Non Patent Literature 1). It is expected that these hepatic growth factors may be used as therapeutic and prophylactic agents efficacious for hepatitis and cirrhosis by increasing normal hepatic parenchymal cells and, because of various biological activities thereof, as curative agents for kidney failure and lesions in stomach, duodenum, skin and the like resulting from side effects of anticancer agents.

A lyophilized formulation comprising hepatic growth factor has been disclosed in Patent Literature 2, which comprises a hepatic growth factor and a stabilizing agent such as glycine, alanine, sorbitol, mannitol or dextran sulfate.

Patent Literature 3 discloses a lyophilized formulation comprising a hepatic growth factor at a concentration as low as less than 5 mg/mL that is suitable for medicaments, the formulation comprising a stabilizing agent such as arginine, lysine, histidine, glutamic acid or aspartic acid.

Patent Literature 4 discloses a lyophilized formulation comprising a hepatic growth factor and a stabilizing agent such as purified sucrose.

CITATION LIST

Patent Literature

[PATENT LITERATURE 1] Patent Publication JP-A-S63-22526
[PATENT LITERATURE 2] Patent Publication JP-A-H9-25241
[PATENT LITERATURE 3] WO 2000/072873
[PATENT LITERATURE 4] WO 2008/102849

Non Patent Literature

[NON PATENT LITERATURE 1] Nature, vol. 342, p. 440-443, 1989

SUMMARY OF THE INVENTION

Problem to be Solved by the Invention

However, the lyophilized formulations comprising hepatic growth factor disclosed in Patent Publication JP-A-H9-25241, WO 2000/072873 and WO 2008/102849 which aimed to increase stability of hepatic growth factor still fail to provide sufficient storage stability.

In addition, it has not been known how to suppress generation of impurities in conjunction with hepatic growth factor or how to keep the pre-storage isoform ratio in lyophilized formulations comprising hepatic growth factor.

Therefore an object of the present invention is to provide a lyophilized formulation having improved storage stability of hepatic growth factor compared to conventional lyophilized formulations.

Means for Solving the Problem

The inventors of the present invention have made intensive studies to achieve the above-described object and, as a result, found that it is possible to achieve the object with a lyophilized formulation comprising (1) a hepatic growth factor, (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof. Thus the inventors have completed the present invention.

The present invention provides the following:

[1] A lyophilized formulation comprising (1) a hepatic growth factor, (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof;

[2] A method for producing a lyophilized formulation, comprising the steps of:

(I) prior to addition of (1) a hepatic growth factor, adjusting pH of an aqueous solution comprising at least (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof, to pH 4.5 to 6.5, and preparing an aqueous solution comprising (1) the hepatic growth factor, (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof; and (II) lyophilizing the aqueous solution comprising the hepatic growth factor obtained in the step (I);

[3] A method for stabilizing a hepatic growth factor by comprising (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof in a lyophilized formulation comprising (1) a hepatic growth factor;

[4] A method for stabilizing a hepatic growth factor by comprising (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof in a lyophilized formulation comprising (1) a hepatic growth factor in order to suppress generation of aggregates of the hepatic growth factor, suppress generation of impurities in conjunction with the hepatic growth factor and/or retain a pre-storage isoform ratio;

[5] A method for stabilizing a hepatic growth factor by comprising (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof in a lyophilized formulation comprising (1) a hepatic growth factor in order to suppress generation of aggregates of the hepatic growth factor;

[6] A method for stabilizing a hepatic growth factor by comprising (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof in a lyophilized formulation comprising (1) a hepatic growth factor in order to suppress generation of impurities in conjunction with the hepatic growth factor;

[7] A method for stabilizing a hepatic growth factor by comprising (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof in a lyophilized formulation comprising (1) a hepatic growth factor in order to retain a pre-storage isoform ratio of the hepatic growth factor; and

[8] The items [1] to [7] as described above, wherein the hepatic growth factor has an amino acid sequence represented by SEQ ID NO: 1.

Advantageous Effect

The present invention can provide a lyophilized formulation having improved storage stability of hepatic growth factor compared to conventional lyophilized formulations.

DESCRIPTION OF EMBODIMENTS

Figure 1:
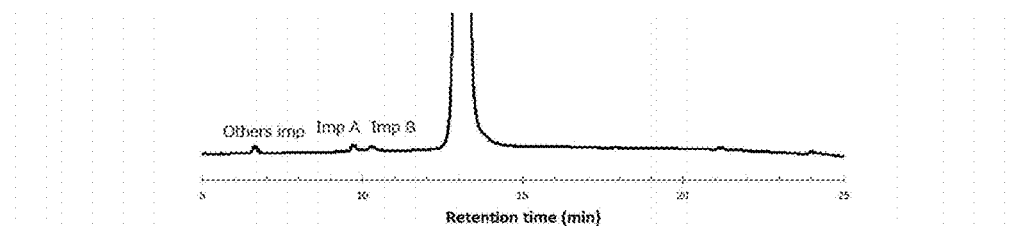
FIG. 1 is a representative chromatogram of impurities in conjunction with hepatic growth factor.

Embodiments of the present invention are hereinafter specifically described. The present invention is not limited to the embodiments described below and may be variously modified within the scope of the invention.

The lyophilized formulation of the present invention comprises (1) a hepatic growth factor, (2) trehalose and (3) one or more compounds (hereinafter also referred to as "the compound (3)") selected from the group consisting of arginine, histidine, lysine, meglumine, glutamic acid, aspartic acid, proline, creatine, creatinine, tris(hydroxymethyl)aminomethane, and pharmaceutically acceptable salts thereof.

A hepatic growth factor for use in the present invention is a protein having the activity of promoting growth of hepatic parenchymal cells and is not particularly limited as far as it is purified to such extent that it can be used as a medicament. For example, Patent Publication JP-A-H11-56382 may be referred.

The hepatic growth factor may be any of those naturally occurring in organ tissue such as liver, spleen and kidney of mammals or in fluidic tissue such as plasma and sera, or those modified having variant amino acid sequences and/or variant carbohydrate chains. Examples of mammals include humans, rats, rabbits, cows, horses, sheep and the like, among which humans are preferred. Examples of the amino acid sequence of human hepatic growth factor include SEQ ID NO: 1.

The hepatic growth factor may be extracted and purified from organ tissue such as liver, spleen and kidney of mammals and from fluidic tissue such as plasma and sera, or isolated from cells producing the hepatic growth factor.

The hepatic growth factor may be obtained by introducing to an appropriate host cell an appropriate vector into which a polynucleotide encoding the hepatic growth factor has been integrated by a genetic engineering technique. The vector is not particularly limited as far as it allows expression of a polynucleotide encoding hepatic growth factor. Examples of the vector include a vector harboring a selection marker that is a gene resistant to antibiotics such as neomycin, a vector harboring a gene encoding dihydrofolate reductase (DHFR) or glutamine synthetase (GS) that can be amplified in animal cells and the like, among which pCI vectors (available from Promega) and pcDNA vectors (available from Invitrogen) are preferred. The host cell is not particularly limited as far as it allows transformation with the vector and expression of a recombinant hepatic growth factor. Examples of the host cell include *Escherichia coli, Bacillus subtilis*, yeasts, filamentous fungi, plant cells, insect cells, animal cells and the like, among which animal cells are preferred and Chinese hamster ovary (CHO) cells are particularly preferred.

The hepatic growth factor obtained by a genetic engineering technique may be, for example, a recombinant hepatic growth factor without particular limitation. For example, Patent Publication JP-A-H3-285693 may be referred. The hepatic growth factor used may be, for example, a recombinant human hepatic growth factor (rhHGF) obtained from a host cell which is a CHO cell.

The hepatic growth factor may be a modified hepatic growth factor which is modified by substitution, deletion, addition or insertion or a combination thereof of one or more, preferably 1 to 10 amino acid residues in the amino acid sequence of a naturally occurring hepatic growth factor within the range that the modified amino acid sequence retains the activity of the hepatic growth factor. The modified hepatic growth factor may be the one having, for example, 80%, preferably 85%, more preferably 90% and still more preferably 95% homology to the amino acid sequence of a naturally occurring hepatic growth factor. For example, WO 90/010651, Patent Publication JP-A-H4-030000 and Patent Publication JP-A-H5-111383 may be referred.

The concentration of the hepatic growth factor before lyophilization is not particularly limited and may be, for example, 5 mg/mL or less, preferably 3 mg/mL or less and more preferably 1 mg/mL or less.

The lyophilized formulation of the present invention is parenterally administered to patients.

When the lyophilized formulation is used for pulmonary administration, the lyophilized formulation of the present invention is dissolved before use and administered to a patient by nebulizer.

When the lyophilized formulation is used for injection, the lyophilized formulation of the present invention is dissolved before use and intravenously, subcutaneously or intramuscularly administered to a patient.

The concentration of the hepatic growth factor in an aqueous solution obtained by dissolving the lyophilized formulation is not particularly limited and may be, for example, 5 mg/mL or less. Water for dissolving the lyophilized formulation of the present invention is not particularly limited as far as it is water used in medical practice and examples thereof include water for injection, sterilized purified water, saline and the like.

Trehalose for use in the present invention is not particularly limited as far as it is purified to a pharmaceutically acceptable extent and examples thereof include trehalose anhydride, trehalose hydrate and the like. Examples of trehalose hydrate include, without particular limitation, trehalose hydrate (trehalose dihydrate) listed in the Japanese Pharmacopoeia 16th edition and the like.

The amount of trehalose added to the lyophilized formulation is such that the mass ratio between the hepatic growth factor and trehalose (hereinafter in this paragraph, expressed as the amount equivalent to trehalose anhydride) is, for example, 1:4 to 1:460, preferably 1:4 to 1:370 and more preferably 1:8 to 1:280. Alternatively, with the total mass of the lyophilized formulation in terms of solid matters being 100.0 parts by mass, trehalose is, for example, 20.0 to 95.0 parts by mass and preferably 30.0 to 94.0 parts by mass. Further, in an aqueous solution comprising 1.0 mg/mL of hepatic growth factor obtained by dissolving the lyophilized formulation, the concentration of trehalose is, for example, 4.0 mg/mL to 460.0 mg/mL and preferably 8.0 mg/mL to 280.0 mg/mL.

The compound (3) for use in the present invention is selected from the group consisting of arginine, histidine, lysine, meglumine, glutamic acid, aspartic acid, proline, creatine, creatinine, tris(hydroxymethyl)aminomethane, and pharmaceutically acceptable salts thereof.

The compound (3) is not particularly limited as far as it is purified to a pharmaceutically acceptable extent. One or two or more kinds of the compound (3) may be used.

The compound (3) is preferably, in view of suppression of generation of aggregations or impurities, one or more selected from the group consisting of arginine, histidine, lysine, glutamic acid, aspartic acid, proline, creatine, creatinine, tris(hydroxymethyl)aminomethane, and pharmaceutically acceptable salts thereof.

The compound (3) includes, as a basic substance, arginine, histidine, lysine and meglumine and is preferably one or more selected from arginine, histidine and lysine. The amount of the compound (3) added to the lyophilized formulation can be within the concentration range that allows dissolution of hepatic growth factor without aggregation in an aqueous solution comprising hepatic growth factor used for production of the lyophilized formulation or in an aqueous solution comprising hepatic growth factor obtained by dissolving the lyophilized formulation.

The amount of the compound (3) added to the lyophilized formulation is such that the mass ratio between the hepatic growth factor and the compound (3) (hereinafter in this paragraph, expressed as the amount equivalent to a free form) is, for example, 1:1 to 1:50, preferably 1:1 to 1:40 and more preferably 1:2 to 1:35. Alternatively, with the total mass of the lyophilized formulation in terms of solid matters being 100.0 parts by mass, the amount of the compound (3) is, for example, 1.5 to 60.0 parts by mass and preferably 3.0 to 59.0 parts by mass. Further, in an aqueous solution comprising 1.0 mg/mL of hepatic growth factor obtained by dissolving the lyophilized formulation, the amount of the compound (3) is, for example, 1.0 mg/mL to 50.0 mg/mL, preferably 1.0 mg/mL to 40.0 mg/mL and more preferably 2.0 mg/mL to 35.0 mg/mL.

The compound (3) in the present invention may be a pharmaceutically acceptable salt thereof. Examples of the pharmaceutically acceptable salt include a hydrochloride, an acetate salt, a sodium salt, a potassium salt, a magnesium salt and the like.

In the present invention, in a lyophilized formulation comprising (1) hepatic growth factor, by further comprising (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof, the storage stability of hepatic growth factor can be improved compared to conventional lyophilized formulations. Storage stability as used herein refers to suppression of generation of aggregates of the hepatic growth factor, suppression of generation of impurities in conjunction with the hepatic growth factor and/or retention of the pre-storage isoform ratio.

The present invention provides a method for stabilizing a hepatic growth factor by comprising (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof in a lyophilized formulation comprising (1) hepatic growth factor.

Namely the present invention provides a method for stabilizing a hepatic growth factor by comprising (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof in a lyophilized formulation comprising (1) hepatic growth factor in order to suppress generation of aggregates of the hepatic growth factor.

The present invention also provides a method for stabilizing a hepatic growth factor by comprising (2) trehalose and (3) one or more compounds selected from the group consisting of arginine, histidine, lysine, meglumine, glutamic acid, aspartic acid, proline, creatine, creatinine, tris (hydroxymethyl)aminomethane, and pharmaceutically acceptable salts thereof in order to suppress generation of impurities in a lyophilized formulation comprising (1) hepatic growth factor in conjunction with the hepatic growth factor.

The present invention further provides a method for stabilizing a hepatic growth factor by comprising (2) trehalose and (3) one or more compounds selected from the group consisting of arginine, histidine, lysine, meglumine, glutamic acid, aspartic acid, proline, creatine, creatinine, tris (hydroxymethyl)aminomethane, and pharmaceutically acceptable salts thereof in a lyophilized formulation comprising (1) hepatic growth factor in order to retain a pre-storage isoform ratio of the hepatic growth factor.

The term "aggregates" as used herein refers to aggregates of hepatic growth factor and examples thereof include soluble aggregates such as dimers and trimers and insoluble aggregates generated by means of interactions.

In the present invention, the amount of aggregates can be evaluated by, for example, measuring the amount of soluble aggregates by size exclusion chromatography.

In the present invention the amount of the soluble aggregates is, when, for example, the amount of aggregates is evaluated for a lyophilized formulation after storage at 60° C. for 1 month by size exclusion chromatography, e.g. less than 1.4% and preferably 1.0% or less. Alternatively, the amount of aggregates measured for a lyophilized formulation after storage at 60° C. for 1 month by size exclusion chromatography is, for example, 4.6 times or less, preferably 4 times or less, more preferably 3.5 times or less and still more preferably 3 times or less of the amount of aggregates before storage.

The amount of insoluble aggregates may be evaluated by, for relatively large insoluble aggregates with the size of 1 µm or more, the light obscuration method in the insoluble particulate matter test described in the Japanese Pharmacopoeia 16th edition or the micro flow imaging method and for insoluble aggregates with the size of 1 µm or less, by the light scattering method or the ultracentrifugation method.

The term "impurity" or "impurities" as used herein refers to one or more substances corresponding to the one or more peaks observed in reverse phase chromatography other than the peak of the hepatic growth factor.

The amount of impurities is evaluated by reverse phase chromatography. For example, for the lyophilized formulations used in Examples in the present specification, two peaks (hereinafter respectively referred to as "ImpA" and "ImpB") at the retention time of around 10 minutes and other impurities than ImpA and ImpB (hereinafter referred to as "Others imp") at the retention time of around 6 to 7 minutes were observed as shown in FIG. 1.

In the present invention the amount of impurities is, when, for example, the amount of impurities is evaluated for a lyophilized formulation after storage at 60° C. for 1 month by reverse phase chromatography, e.g. 1.7% or less, preferably 1.5% or less, more preferably 1.3% or less and still more preferably 1.0% or less. Alternatively, the amount of impurities measured for a lyophilized formulation after storage at 60° C. for 1 month by reverse phase chromatography is, for example, less than 9 times, more preferably 7 times or less, more preferably 5 times or less and still more preferably 3 times or less of the amount of impurities before storage.

The term "isoform" as used herein refers to a charge variant of hepatic growth factor and refers to a plurality of proteins having different charge state.

Figure 2:
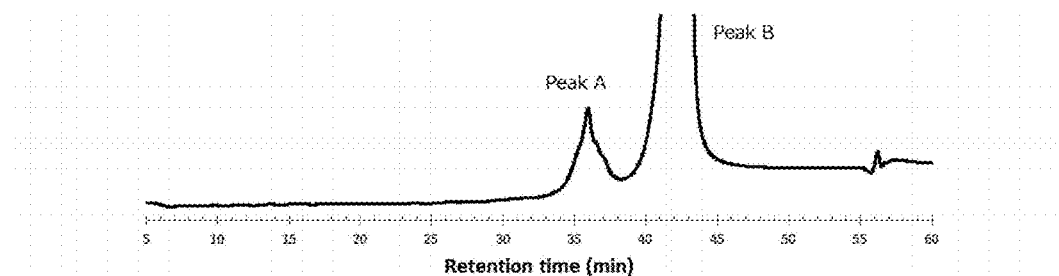
FIG. 2 is a representative chromatogram of isoforms of hepatic growth factor.

The isoform ratio can be evaluated, for example, by ion exchange chromatography. For example, for the lyophilized formulations used in Examples in the present specification, two peaks (hereinafter respectively referred to as "peak A" and "peak B") were observed at 35 to 45 minutes of retention time as shown in FIG. 2. The term "isoform ratio" as used herein refers to the proportion of each isoform with respect to the total amount of isoforms.

Biological activity of hepatic growth factor in the present invention can be evaluated according to a cell-based assay which evaluates proliferation of mink lung epithelial cells (Mv.1.Lu cells) or 4BMr5 cells in the presence of transforming growth factor β-1 (TGFβ-1) (see Journal of Immnological Methods. vol. 258, p. 1-11, 2001 and the like) and can be expressed as the 50% effective concentration (EC50). The change in the biological activity of the lyophilized formulation during storage can be expressed as the relative titer (%) obtained by dividing EC50 before storage by EC50 after storage.

In order to keep constant pH of an aqueous solution comprising hepatic growth factor used for production of the lyophilized formulation or of an aqueous solution comprising hepatic growth factor obtained by dissolving the lyophilized formulation, the lyophilized formulation may comprise a buffering agent.

The buffering agent for use in the present invention is not particularly limited as far as it is pharmaceutically acceptable and examples thereof include phosphoric acid, sodium dihydrogen phosphate, sodium dihydrogen phosphate monohydrate, citric acid hydrates, sodium citrate hydrates, disodium citrate, acetic acid, glacial acetic acid, sodium acetate hydrates, sodium carbonate hydrates, sodium hydrogen carbonate, glycine, glycylglycine and the like.

The buffering agent may be used in the form of a buffer solution which is generally used such as phosphate buffer solution, citric acid buffer solution and acetic acid buffer solution.

The amount of the buffering agent in the lyophilized formulation is, in terms of the concentration in an aqueous solution comprising hepatic growth factor before lyophilization, e.g. 1 to 100 mM. By adjusting the concentration to this range, constant pH of the aqueous solution comprising hepatic growth factor obtained by dissolving the lyophilized formulation can be achieved.

Hepatic growth factor has varied solubility depending on pH, with the solubility being at a minimum at around the isoelectric point. Therefore pH may be selected, while taking the isoelectric point into account, so that hepatic growth factor can be dissolved without aggregation in an aqueous solution comprising hepatic growth factor used for production of the lyophilized formulation or in an aqueous solution comprising hepatic growth factor obtained by dissolving the lyophilized formulation.

In the present invention, the hepatic growth factor used in Examples in the present specification for example has the minimal solubility of 0.1 to 0.2 mg/mL at around neutral pH which is the isoelectric point and has the solubility of 1.6 mg/mL or higher at around pH 5. Therefore an aqueous solution before lyophilization and an aqueous solution obtained by dissolving the lyophilized formulation has pH of, for example, 4.5 to 6.5 and preferably 5.0 to 6.0.

In the method for producing a lyophilized formulation of hepatic growth factor of the present invention, a pH adjusting agent other than the buffering agent may be used in order to adjust pH of an aqueous solution before lyophilization.

The pH adjusting agent for use in the present invention is not particularly limited as far as it is pharmaceutically acceptable and examples thereof include hydrochloric acid, anhydrous citric acid, citric acid hydrates, sodium citrate hydrates, glycine, succinic acid, acetic acid, glacial acetic acid, sodium acetate hydrates, tartaric acid, sodium hydroxide, sodium hydrogen carbonate, sodium carbonate hydrates, dried sodium carbonate, monoethanolamine, triethanolamine, lactic acid, sodium lactate, phosphoric acid, sodium hydrogen phosphate hydrates, anhydrous sodium monohydrogen phosphate, sodium dihydrogen phosphate, anhydrous sodium dihydrogen phosphate, crystalline sodium dihydrogen phosphate, trisodium phosphate, dipotassium phosphate, potassium dihydrogen phosphate and the like.

In order to prevent reduction of the content of hepatic growth factor in a drug solution to be administered due to adsorption of the hepatic growth factor to glass or resin constituting a container after reconstitution of the lyophilized formulation, the lyophilized formulation may comprise a surfactant.

The surfactant for use in the present invention is not particularly limited as far as it is pharmaceutically acceptable and examples thereof include nonionic surfactants specifically including polysorbate 80, polysorbate 20, poloxamers, polyethylene glycols, HCO-40, HCO-60 and the like.

The amount of the surfactant in the lyophilized formulation is, in an aqueous solution comprising 1.0 mg/mL of hepatic growth factor obtained by dissolving the lyophilized formulation, e.g. 0.020 to 1.0 mg/mL, preferably 0.050 to 1.0 mg/mL, more preferably 0.075 to 0.5 mg/mL and still more preferably 0.075 to 0.2 mg/mL.

The lyophilized formulation of the present invention comprises, with the total mass of the lyophilized formulation in terms of solid matters being 100.0 parts by mass, 0.1 to 4.5 parts by mass of the hepatic growth factor, 20.0 to 95.0 parts by mass of trehalose (hereinafter in this paragraph, expressed as the amount equivalent to trehalose anhydride) and 1.5 to 60.0 parts by mass of the compound (3) (hereinafter in this paragraph, expressed as the amount equivalent to a free form). In one embodiment, with the total mass of the lyophilized formulation in terms of solid matters being 100.0 parts by mass, the hepatic growth factor accounts for 0.3 to 4.4 parts by mass, trehalose accounts for 30.0 to 94.0 parts by mass and the compound (3) accounts for 3.0 to 59.0 parts by mass. In another embodiment, hepatic growth factor accounts for 0.3 to 4.4 parts by mass, trehalose accounts for 30.0 to 94.0 parts by mass, the compound (3) accounts for 3.0 to 59.0 parts by mass and polysorbate 80 accounts for 0.026 to 0.7 parts by mass.

In the present invention, the lyophilized formulation may further comprise, if necessary, an additive such as a vehicle, a tonicity agent and an antioxidant.

A method for producing a lyophilized formulation of the present invention comprises the steps of:

(I) prior to addition of (1) a hepatic growth factor, adjusting pH of an aqueous solution comprising at least (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof, to pH 4.5 to 6.5, and preparing an aqueous solution comprising (1) the hepatic growth factor, (2) trehalose and (3) one or more compounds selected from the group consisting of arginine, histidine, lysine, meglumine, glutamic acid, aspartic acid, proline, creatine, creatinine, tris(hydroxymethyl)aminomethane, and pharmaceutically acceptable salts thereof; and (II) lyophilizing the aqueous solution comprising the hepatic growth factor obtained in the step (I).

The lyophilized formulation of the present invention can be produced by the production method.

In the step (I), pH of an aqueous solution comprising at least (3) one or more compounds selected from the group consisting of arginine, histidine, lysine, meglumine, glutamic acid, aspartic acid, proline, creatine, creatinine, tris (hydroxymethyl)aminomethane, and pharmaceutically acceptable salts thereof is adjusted to pH 4.5 to 6.5 and preferably to pH 5.0 to 6.0.

Prior to adjusting pH, the aqueous solution may comprise (2) trehalose but does not comprise (1) hepatic growth factor. Namely after adjusting pH of the aqueous solution comprising at least the compound (3) to pH 4.5 to 6.5, (1) hepatic growth factor is added thereto or (1) hepatic growth factor and (2) trehalose are simultaneously or sequentially added thereto.

In order to adjust pH, a buffering agent and/or a pH adjusting agent can be used. Reaction temperature during adjusting pH is not particularly limited.

The aqueous solution comprising at least the compound (3) can be prepared by dissolving the compound (3) in a solvent.

The solvent for preparation of the aqueous solution comprising at least the compound (3) is not particularly limited as far as it is, for example, pharmaceutically acceptable water. Examples thereof include water for injection, sterilized purified water and the like.

(1) Hepatic growth factor and (2) trehalose may be added as they are or in the form of aqueous solution. A solvent for preparing an aqueous solution may be the same as or different from the solvent for preparation of the aqueous solution comprising at least the compound (3). Temperature during addition of (1) hepatic growth factor and (2) trehalose is not particularly limited.

In the step (I), a surfactant, other additives (a vehicle, a tonicity agent, an antioxidant and the like) and the like may be added, if necessary.

In the step (II), the aqueous solution comprising the hepatic growth factor obtained in the step (I) is lyophilized.

The aqueous solution comprising the hepatic growth factor can be lyophilized according to a common method after pouring the aqueous solution comprising the hepatic growth factor into a vial or an ampoule.

It is preferred that the aqueous solution comprising the hepatic growth factor is sterilized by filtration through a filter or the like and lyophilized.

Examples of the lyophilization method include a method comprising three unit operations of a freezing step for cooling and freezing under normal pressure, a primary drying step for sublimation and drying of free water which is not engaged to solutes under reduced pressure and a secondary drying step for removing adsorbed water and crystallization water inherent to the solutes (for reference, Pharm. Tech. Japan, vol. 8, no. 1, p. 75-87, 1992 and the like may be mentioned).

The temperature during the freezing step is, for example, −40° C. or less. The temperature during the primary drying step is, for example, −20° C. to 10° C. The temperature during the secondary drying step is, for example, 20° C. to 30° C. The reduced pressure is, for example, 10 Pa or less.

The term "cake" as used herein refers to a porous solid matter in the lyophilized formulation. Characteristics of the lyophilized formulation can be evaluated by visual observation of the porous structure or color of a cake or solubility of the lyophilized formulation in water or visual observation of the thus obtained aqueous solution.

The lyophilized formulation of the present invention is generally an acceptably white cake and is rapidly dissolved in water to give a clear and colorless aqueous solution.

On the other hand, an aqueous solution obtained by dissolving a conventional lyophilized formulation may be turbid potentially due to generation of insoluble aggregates which may be derived from hepatic growth factor and the like. Thus the characteristics of the aqueous solution obtained by dissolving the lyophilized formulation may be indicative of generation of insoluble aggregates. The fact that the aqueous solution is clear after storage of the lyophilized formulation means that generation of insoluble aggregates is suppressed.

EXAMPLES

The present invention is hereinafter more specifically described by way of Examples which do not limit the present invention.

Hepatic growth factor used in the present Examples was prepared by fully synthesizing a gene on the basis of amino acid sequence information disclosed in Patent Publication JP-A-H11-056382, incorporating the gene in a vector, expressing the protein in CHO cells and isolating and purifying the protein.

Examples 1 to 25 and Comparative Examples 1 to 7

Lyophilized formulations of Examples and Comparative Examples were prepared by the method described hereinbelow. Tables 1 to 4 indicate the amounts (mg) of components per mL of each aqueous solution comprising hepatic growth factor. The values in Tables are rounded to one decimal place. The aqueous solutions comprising hepatic growth factor were prepared in the volume ranging from 100 mL to 250 mL.

TABLE 1

| | Examples | | | | Comparative Examples | | | | | |
|---|---|---|---|---|---|---|---|---|---|---|
| | 1 | 2 | 3 | 4 | 1 | 2 | 3 | 4 | 5 | 6 |
| Hepatic growth factor | 1.0 | 1.0 | 1.0 | 1.0 | 1.0 | 1.0 | 1.0 | 1.0 | 1.0 | 1.1 |
| Trehalose dihydrate | 100.0 | 100.0 | 100.0 | 100.0 | — | — | — | — | — | — |
| Xylitol | — | — | — | — | 100.0 | — | — | — | — | — |
| Sucrose | — | — | — | — | — | 100.0 | — | — | — | 10.0 |
| Sorbitol | — | — | — | — | — | — | 100.0 | — | — | — |
| Mannitol | — | — | — | — | — | — | — | 100.0 | — | — |
| L-arginine | 17.4 | — | — | — | 17.4 | 17.4 | 17.4 | 17.4 | 17.4 | — |
| L-histidine | — | 15.5 | — | — | — | — | — | — | — | — |
| L-lysine | — | — | 14.6 | — | — | — | — | — | — | — |
| Meglumine | — | — | — | 19.5 | — | — | — | — | — | — |
| L-alanine | — | — | — | — | — | — | — | — | — | 5.0 |
| Sodium chloride | — | — | — | — | — | — | — | — | 9.0 | 18.0 |
| Citric acid monohydrate | | | | | | | 2.1 | | | |
| Polysorbate 80 | | | | | | | 0.1 | | | 0.3 |

TABLE 2

| | Examples | | | | | | |
|---|---|---|---|---|---|---|---|
| | 5 | 6 | 7 | 8 | 9 | 10 | 11 |
| Hepatic growth factor | 1.1 | 1.1 | 1.1 | 1.1 | 1.1 | 1.1 | 1.1 |
| Trehalose dihydrate | | | | 100.0 | | | |
| L-arginine | 4.2 | — | — | — | — | — | — |
| L-arginine hydrochloride | 16.0 | — | — | — | — | — | — |
| Sodium glutamate | — | 18.7 | — | — | — | — | — |
| Sodium aspartate | — | — | 17.7 | — | — | — | — |
| Proline | — | — | — | 11.5 | — | — | — |
| Creatine | — | — | — | — | 14.9 | — | — |
| Creatinine | — | — | — | — | — | 11.3 | — |
| Tris(hydroxymethyl)aminomethane | — | — | — | — | — | — | 12.1 |
| Citric acid monohydrate | | | | 2.1 | | | |
| Polysorbate 80 | | | | 0.1 | | | |

TABLE 3

| | Examples | | | | | | |
|---|---|---|---|---|---|---|---|
| | 12 | 13 | 14 | 15 | 16 | 17 | 18 |
| Hepatic growth factor | 0.5 | 1.0 | 3.1 | 5.1 | 1.1 | 1.0 | 1.0 |
| Trehalose dihydrate | 100.0 | 100.0 | 100.0 | 100.0 | 10.0 | 25.0 | 50.0 |
| L-arginine | 5.5 | 6.8 | 12.1 | 17.4 | 4.2 | 4.2 | 4.2 |
| L-arginine hydrochloride | 14.4 | 12.8 | 6.4 | — | 16.0 | 16.0 | 16.0 |
| Citric acid monohydrate | | | | 2.1 | | | |
| Polysorbate 80 | | | | 0.1 | | | |

TABLE 4

| | Examples | | | | | | | Comparative Example 7 |
|---|---|---|---|---|---|---|---|---|
| | 19 | 20 | 21 | 22 | 23 | 24 | 25 | |
| Hepatic growth factor | 1.0 | 1.0 | 1.1 | 1.1 | 1.1 | 1.1 | 1.1 | 1.1 |
| Trehalose dihydrate | 150.0 | 200.0 | 250.0 | 300.0 | 100.0 | 100.0 | 100.0 | — |

TABLE 4-continued

| | Examples | | | | | | | Comparative |
|---|---|---|---|---|---|---|---|---|
| | 19 | 20 | 21 | 22 | 23 | 24 | 25 | Example 7 |
| L-arginine | 4.2 | 4.2 | 4.2 | 4.2 | 3.5 | 8.7 | 26.1 | 4.2 |
| L-arginine hydrochloride | 16.0 | 16.0 | 16.0 | 16.0 | — | — | — | 16.0 |
| Citric acid monohydrate | | | | | 2.1 | | | |
| Polysorbate 80 | | | | | 0.1 | | | |

<Preparation of Mixing Buffer>

According to the volume of each aqueous solution comprising hepatic growth factor and the concentration indicated in Tables 1 to 4, components other than hepatic growth factor or polysorbate 80 were mixed and stirred with an appropriate amount of water for injection (about 80% of the volume of the aqueous solution comprising hepatic growth factor). After visually confirming the dissolution, the pH was adjusted to 5.5 with hydrochloric acid and/or sodium hydroxide and the volume was adjusted with water for injection to give a mixing buffer.

<Preparation of Aqueous Solution Comprising Hepatic Growth Factor>

An aqueous solution comprising hepatic growth factor was prepared by the following procedure.

(a) An aqueous solution comprising hepatic growth factor was adjusted so as to have the concentration of the hepatic growth factor as indicated in Table 1 by ultrafiltration using the above mixing buffer. The concentration of hepatic growth factor was calculated from the following formula (A) after determining the absorbance at 280 nm on an ultraviolet-visible spectrophotometer (using a cell with a light path of 1 cm):

$$\text{Protein concentration (mg/mL)} = (A280/1.73) \times D \quad (A)$$

wherein:

A280: absorbance at 280 nm;

1.73: theoretical absorbance of a sample solution with 0.1% concentration with the light path of 1 cm and at 280 nm; and D: dilution factor upon measurement.

(b) Thereafter polysorbate 80 was added so as to obtain the desired concentration as indicated in Table 1 followed by filtration through a sterile filter (product name: MILLEX GV 0.22 μm filter, available from Millipore) to give the aqueous solution comprising hepatic growth factor.

<Lyophilization Step>

The aqueous solution comprising hepatic growth factor was divided at 1 mL into 5-mL glass vials which were then partially closed with rubber caps. After lyophilization according to the program indicated in Table 5, each vial was completely closed with the rubber cap. An aluminum cap was then attached to the glass vial to give a lyophilized formulation.

Comparative Example 5 is a lyophilized formulation produced according to the formulation disclosed in WO 2000/072873. Comparative Example 6 is a lyophilized formulation produced according to the formulation disclosed in WO 2008/102849.

TABLE 5

| | Freezing | Hold freezing | Pressure reduction | Heating | Primary drying | Heating | Secondary drying |
|---|---|---|---|---|---|---|---|
| Temperature (° C.) | Room temp. → −40 | −40 | −40 | −40 → −20 | −20 | −20 → 20 | 20 |
| Pressure (Pa) | Normal pressure | Normal pressure | Normal pressure → 10 | 10 | 10 | 10 | 10 |
| Time (h) | 1.5 | 4 | 1 | 2 | 48 | 8 | 48 |

Test Example 1

The obtained lyophilized formulations of Examples 1 to 11 and Comparative Examples 1 to 6 were examined for characteristics of the lyophilized formulations, solubility of the lyophilized formulations in water for injection and characteristics of the aqueous solutions obtained after dissolution according to the following procedures.

<Method>

Each obtained lyophilized formulation was visually observed (formation of cake and color hue) in white and black backgrounds in an environment with 1000 to 3000 lux. Water for injection (1 mL) was then added to each lyophilized formulation which was then left to stand before visual observation of solubility of the lyophilized formulation and color of the obtained solution.

The term "instant" indicated in Table 6 refers to that the formulation was completely dissolved within 1 minute and the term "slightly soluble" refers to that the formulation was not completely dissolved even after 1 minute.

<Results>

The results for the samples of Examples 1 to 4 and Comparative Examples 1 to 6 are shown in Table 6. Examples 1 to 4 formed white cakes and showed preferable solubility. Comparative Example 1 comprising xylitol and Comparative Example 3 comprising sorbitol did not form cakes and were white or colorless molten solids. Comparative Example 5 which did not comprise a saccharide was a white solid without formation of a cake that is generally observed for lyophilized formulations. Examples 5 to 11 also formed white cakes similarly to Examples 1 to 4 and showed preferable solubility.

TABLE 6

| | Formation of cake | Color of cake | Solubility | Color of solution |
|---|---|---|---|---|
| Example 1 | Good | White | Instant | Clear |
| Example 2 | Good | White | Instant | Clear |
| Example 3 | Good | White | Instant | Clear |
| Example 4 | Good | White | Instant | Clear |

TABLE 6-continued

| | Formation of cake | Color of cake | Solubility | Color of solution |
|---|---|---|---|---|
| Comparative Example 1 | No | Colorless | Slightly soluble | Clear |
| Comparative Example 2 | Good | White | Instant | Clear |
| Comparative Example 3 | No | White | Slightly soluble | Clear |
| Comparative Example 4 | Good | White | Instant | Clear |
| Comparative Example 5 | No | White | Instant | Clear |
| Comparative Example 6 | Good | White | Instant | Clear |

The obtained lyophilized formulations were stored in a thermostatic chamber at 25° C., 40° C. or 60° C. for 2 weeks or 1 month followed by the following tests.

Test Example 2

The amount of soluble aggregates in Examples 1 to 25 and Comparative Examples 1 to 7 was evaluated as follows.
<Method>
Water for injection (1 mL) was added to each lyophilized formulation of Example and Comparative Example for dissolution under ice cooling. The solution was moderately shaken to obtain a uniform solution which was then left to stand for 5 minutes. The obtained solution was distributed into 250-μL vial inserts which were placed in HPLC vials to obtain samples.

Figure 3:
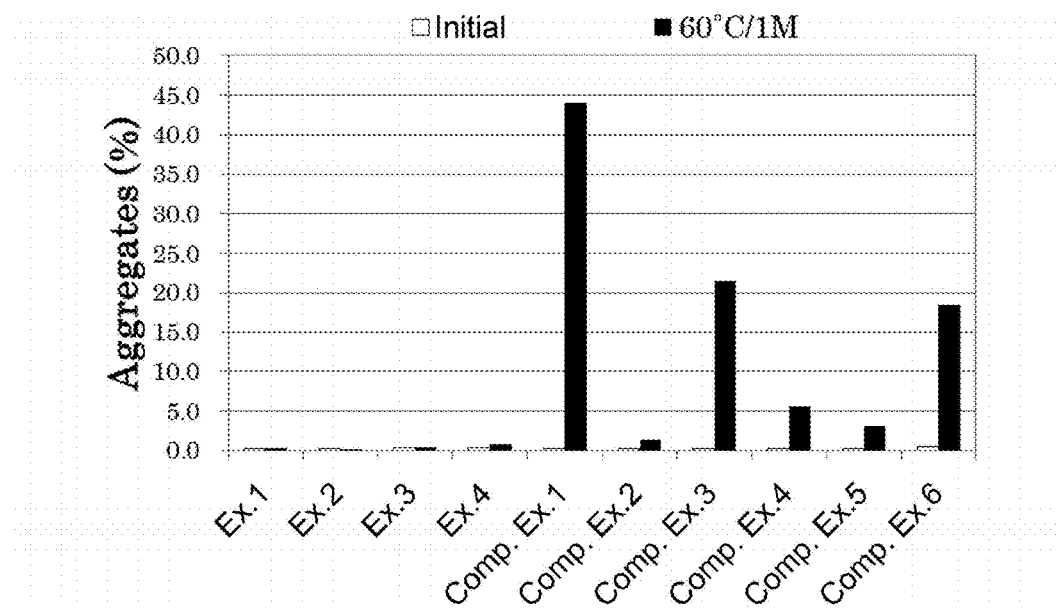
FIG. 3 shows the amount of soluble aggregates in lyophilized formulations tested in Test Example 2 initially and after storage at 60° C. for 1 month.

Each sample was measured by size exclusion chromatography under the following analytical conditions for the amount of soluble aggregates before and after storage and the amount of soluble aggregates was calculated by the area percentage method.
Detector: UV 280 nm;
Column: guard column (trade name: TSKgel G3000SWXL, available from Tosoh Corporation);
Column temperature: 30° C.;
Mobile phase: obtained by dissolving 39 g of sodium dihydrogen phosphate dihydrate, 87.5 g of sodium chloride and 5.0 g of sodium lauryl sulfate in 5000 mL of water and adjusting pH of the solution to 7.5 with a 2 mol/L sodium hydroxide solution;
Sample injection: 50 μL; and
Flow rate: 1 mL/min.
<Results>
The results of measurement of the amount of soluble aggregates in samples initially (before storage) and after storage at 25° C., 40° C. or 60° C. for 2 weeks or 1 month are shown in Tables 7 to 9. The results of measurement of the amount of soluble aggregates in samples of Examples 1 to 4 and Comparative Examples 1 to 6 initially and after storage at 60° C. for 1 month are shown in FIG. 3. Further, the correlation between the content of trehalose in lyophilized formulations and the amount of soluble aggregates is shown in Table 10.

According to Table 7, the amount of soluble aggregates in Comparative Examples 1 to 6 was increased with an increase in the storage period and storage temperature. The amount of soluble aggregates was significantly increased after storage at 60° C. for 1 month.

According to Tables 7 and 8 meanwhile, such a significant change in the amount of soluble aggregates as in Comparative Examples was not observed for Examples 1 to 11 under the storage conditions tested. Thus generation of soluble aggregates was suppressed in Examples 1 to 11 even under the storage condition of 60° C.

According to Tables 9 and 10, the amount of soluble aggregates was significantly increased in Comparative Example 7 which did not comprise trehalose.

Meanwhile no significant change in the amount of soluble aggregates was observed for Examples 12 to 15 comprising various amounts of hepatic growth factor and Examples 23 to 25 comprising various amounts of arginine.

TABLE 7

| | Amount of aggregates (%) | | | | | |
|---|---|---|---|---|---|---|
| | | 2-week storage | | | 1-month storage | | |
| | Initial | 25° C. storage | 40° C. storage | 60° C. storage | 25° C. storage | 40° C. storage | 60° C. storage |
| Example 1 | 0.3 | 0.2 | 0.2 | 0.2 | 0.2 | 0.2 | 0.3 |
| Example 2 | 0.2 | 0.2 | 0.2 | 0.2 | 0.2 | 0.2 | 0.2 |
| Example 3 | 0.3 | 0.4 | 0.4 | 0.4 | 0.3 | 0.3 | 0.4 |
| Example 4 | 0.3 | 0.3 | 0.3 | 0.3 | 0.3 | 0.3 | 0.8 |
| Comparative Example 1 | 0.3 | 0.6 | 1.1 | 26.4 | 0.8 | 1.6 | 44.1 |
| Comparative Example 2 | 0.3 | 0.3 | 0.3 | 0.6 | 0.3 | 0.3 | 1.4 |
| Comparative Example 3 | 0.3 | 0.3 | 0.7 | 11.5 | 0.4 | 0.9 | 21.5 |
| Comparative Example 4 | 0.3 | 0.3 | 0.3 | 1.9 | 0.3 | 0.4 | 5.6 |
| Comparative Example 5 | 0.3 | 0.3 | 0.4 | 1.9 | 0.4 | 0.4 | 3.1 |
| Comparative Example 6 | 0.4 | 0.8 | 1.1 | 6.8 | 1.0 | 1.4 | 18.4 |

TABLE 8

| | Amount of aggregates (%) | |
|---|---|---|
| | Initial | 60° C./2-week storage |
| Example 5 | 0.2 | 0.2 |
| Example 6 | 0.2 | 0.3 |
| Example 7 | 0.3 | 0.3 |
| Example 8 | 0.2 | 0.2 |
| Example 9 | 0.2 | 0.3 |
| Example 10 | 0.2 | 0.2 |
| Example 11 | 0.2 | 0.3 |

TABLE 9

| | Amount of aggregates (%) | | | |
|---|---|---|---|---|
| | | 1-month storage | | |
| | Initial | 25° C. storage | 40° C. storage | 60° C. storage |
| Example 12 | 0.3 | 0.2 | 0.2 | 0.2 |
| Example 13 | 0.2 | 0.2 | 0.2 | 0.2 |
| Example 14 | 0.2 | 0.3 | 0.2 | 0.2 |
| Example 15 | 0.2 | 0.2 | 0.3 | 0.3 |
| Example 16 | 0.2 | 0.2 | 0.2 | 0.6 |
| Example 17 | 0.2 | 0.2 | 0.2 | 0.4 |
| Example 18 | 0.2 | 0.2 | 0.3 | 0.2 |
| Example 19 | 0.2 | 0.3 | 0.2 | 0.3 |
| Example 20 | 0.2 | 0.2 | 0.2 | 0.2 |
| Example 21 | 0.2 | 0.2 | 0.2 | 0.2 |
| Example 22 | 0.2 | 0.2 | 0.2 | 0.2 |
| Example 23 | 0.2 | 0.2 | 0.3 | 0.3 |
| Example 24 | 0.2 | 0.3 | 0.2 | 0.3 |

TABLE 9-continued

| | Amount of aggregates (%) | | | |
|---|---|---|---|---|
| | | 1-month storage | | |
| | Initial | 25° C. storage | 40° C. storage | 60° C. storage |
| Example 25 | 0.3 | 0.2 | 0.2 | 0.2 |
| Comparative Example 7 | 0.2 | 0.2 | 0.2 | 1.5 |

TABLE 10

| | | Amount of aggregates (%) | | | |
|---|---|---|---|---|---|
| | Trehalose | | 1-month storage | | |
| | conc. (mg/mL) | Initial | 25° C. storage | 40° C. storage | 60° C. storage |
| Comparative Example 7 | 0 | 0.2 | 0.2 | 0.2 | 1.5 |
| Example 16 | 10 | 0.2 | 0.2 | 0.2 | 0.6 |
| Example 17 | 25 | 0.2 | 0.2 | 0.2 | 0.4 |
| Example 18 | 50 | 0.2 | 0.2 | 0.3 | 0.2 |
| Example 13 | 100 | 0.2 | 0.2 | 0.2 | 0.2 |
| Example 19 | 150 | 0.2 | 0.3 | 0.2 | 0.3 |
| Example 20 | 200 | 0.2 | 0.2 | 0.2 | 0.2 |
| Example 21 | 250 | 0.2 | 0.2 | 0.2 | 0.2 |
| Example 22 | 300 | 0.2 | 0.2 | 0.2 | 0.2 |

Test Example 3

The amount of impurities in Examples 1 to 25 and Comparative Examples 1 to 7 was evaluated as follows.
<Method>
The samples used were those in HPLC vials prepared for evaluation of the amount of soluble aggregates.

Figure 4:
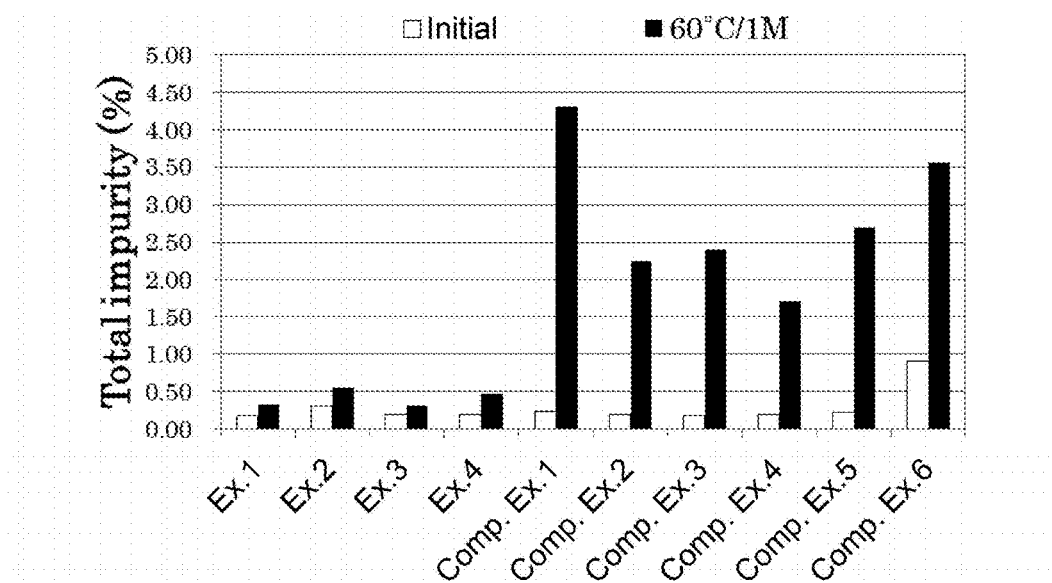
FIG. 4 shows the total amount of impurities in lyophilized formulations tested in Test Example 3 initially and after storage at 60° C. for 1 month.

Each sample was measured by reverse phase chromatography under the following analytical conditions for the amount of impurities before and after storage and the amount of impurities was calculated by the area percentage method.
Detector: UV 215 nm;
Column: reverse phase column (trade name: Inertsil WP300-C8, available from GL Sciences Inc.) attached with the GL Cart guard column;
Column temperature: 40° C.;
Mobile phase A: water/trifluoroacetic acid (1000:1);
Mobile phase B: acetonitrile/trifluoroacetic acid (1000:0.85);
Sample injection: 25 μL;
Flow rate: 1 mL/min; and
Gradient: the volume ratio of the mobile phase B with respect to the total amount of the mobile phase A and the mobile phase B: 15% (Initial)-70% (27.5 min)-70% (30 min)-15% (30.01 min)-15% (35 min).
<Results>
The results of measurement of the amount of impurities in samples of Examples 1 to 11 and Comparative Examples 1 to 6 initially (before storage) and after storage at 25° C., 40° C. or 60° C. for 2 weeks or 1 month are shown in Tables 11 and 12. The results of measurement of the total amount of impurities in samples of Examples 1 to 4 and Comparative Examples 1 to 6 initially and after storage at 60° C. for 1 month are shown in FIG. 4.

According to Table 11, the total amount of impurities in Examples 1 to 4 was not substantially changed under the storage conditions of 25° C. and 40° C. According to Tables 11 and 12, an increase in the total amount of impurities in Examples 1 to 11 was at most 2-fold relative to the initial value even under the storage condition of 60° C., while an increase in the amount in formulations of all Comparative Examples was almost 10-fold or more. Under the storage condition of 60° C., it was found that any of ImpA, ImpB and Others imp was increased in formulations of all Comparative Examples. Thus generation of impurities was suppressed in Examples 1 to 11 even under the storage condition of 60° C.

In Examples 12 to 25, no significant change in the total amount of impurities was observed under any storage conditions.

TABLE 11

| | Total amount of impurities (%) | | | | | | |
|---|---|---|---|---|---|---|---|
| | | 2-week storage | | | 1-month storage | | |
| | Initial | 25° C. storage | 40° C. storage | 60° C. storage | 25° C. storage | 40° C. storage | 60° C. storage |
| Example 1 | 0.18 | 0.19 | 0.19 | 0.36 | 0.20 | 0.20 | 0.32 |
| Example 2 | 0.31 | 0.33 | 0.34 | 0.55 | 0.33 | 0.35 | 0.55 |
| Example 3 | 0.20 | 0.28 | 0.21 | 0.41 | 0.61 | 0.23 | 0.32 |
| Example 4 | 0.19 | 0.20 | 0.21 | 0.42 | 0.20 | 0.20 | 0.47 |
| Comparative Example 1 | 0.23 | 0.51 | 0.74 | 2.34 | 0.38 | 0.50 | 4.31 |
| Comparative Example 2 | 0.20 | 0.19 | 0.68 | 0.95 | 0.19 | 0.21 | 2.25 |
| Comparative Example 3 | 0.19 | 0.21 | 0.31 | 1.42 | 0.28 | 0.48 | 2.40 |
| Comparative Example 4 | 0.19 | 0.20 | 0.48 | 0.89 | 0.29 | 0.31 | 1.71 |
| Comparative Example 5 | 0.22 | 0.35 | 0.43 | 1.02 | 0.23 | 0.49 | 2.69 |
| Comparative Example 6 | 0.91 | 1.58 | 1.75 | 2.86 | 1.84 | 2.11 | 3.56 |

TABLE 12

| | Total amount of impurities (%) | |
|---|---|---|
| | Initial | 60° C./2-week storage |
| Example 5 | 0.21 | 0.38 |
| Example 6 | 0.20 | 0.41 |
| Example 7 | 0.21 | 0.34 |
| Example 8 | 0.21 | 0.36 |
| Example 9 | 0.20 | 0.38 |
| Example 10 | 0.21 | 0.39 |
| Example 11 | 0.20 | 0.39 |

Test Example 4

The isoform ratio in Examples 1 to 25 and Comparative Examples 1 to 7 was evaluated as follows.
<Method>
The samples used were those in HPLC vials prepared for evaluation of the amount of aggregates.

Each sample was measured by ion exchange chromatography under the following analytical conditions for the amount of isoforms before and after storage and the isoform ratio was calculated by the area percentage method.
Detector: UV 215 nm;
Column: trade name: Agilent Bio SCX NP5 PK, available from Agilent Technologies;
Column temperature: 30° C.;
Mobile phase A: 50 mmol/L Tris-HCl buffer (pH 9.0);
Mobile phase B: 50 mmol/L Tris-HCl buffer (pH 9.0), 1 mol/L NaCl Sample injection: 50 μL;
Flow rate: 0.5 mL/min; and
Gradient: the volume ratio of the mobile phase B with respect to the total amount of the mobile phase A and the mobile phase B: 20% (Initial)-60% (50 min)-80% (51 min)-80% (60 min)-20% (60.01 min)-20% (80 min).

<Results>

Figure 5:
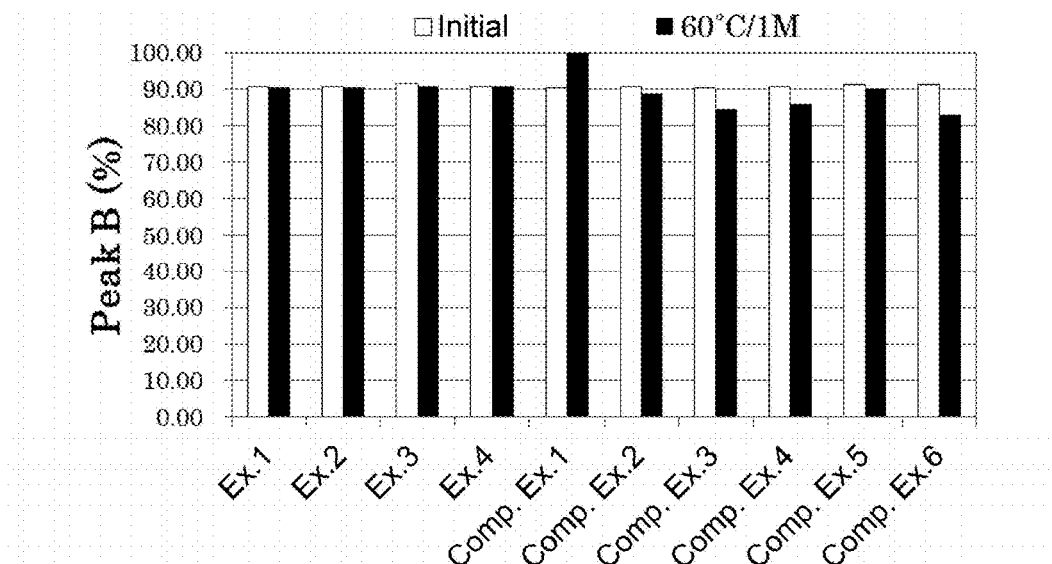
FIG. 5 shows the ratio of peak B with respect to isoforms in lyophilized formulations tested in Test Example 4 initially and after storage at 60° C. for 1 month.

The results of measurement of change in the amount of isoforms expressed as the ratio of peak B with respect to the sum of peak A and peak B in samples initially (before storage) and after storage at 25° C., 40° C. or 60° C. for 2 weeks or 1 month are shown in Tables 13 to 15. The results of measurement of change in the isoform ratio expressed as the ratio of peak B in samples of Examples 1 to 4 and Comparative Examples 1 to 6 initially and after storage at 60° C. for 1 month are shown in FIG. 5. Further, the correlation between the content of trehalose in lyophilized formulations and the ratio of peak B is shown in FIG. 6 and the correlation between the content of arginine and the ratio of peak B is shown in FIG. 7.

According to Tables 13 and 14, little change in the isoform ratio of peak B was observed in Examples 1 to 11 and Comparative Example 5 under the storage conditions tested, while the isoform ratio of peak B was significantly changed in other Comparative Examples under the storage condition of 60° C. Thus change in the isoform ratio was suppressed in Examples 1 to 11 even under the storage condition of 60° C. In Comparative Example 1, a significant change was observed after storage, namely the isoform of peak A was eliminated, so that only the isoform detected was peak B and a peak which was not an isoform was observed.

Figure 6:
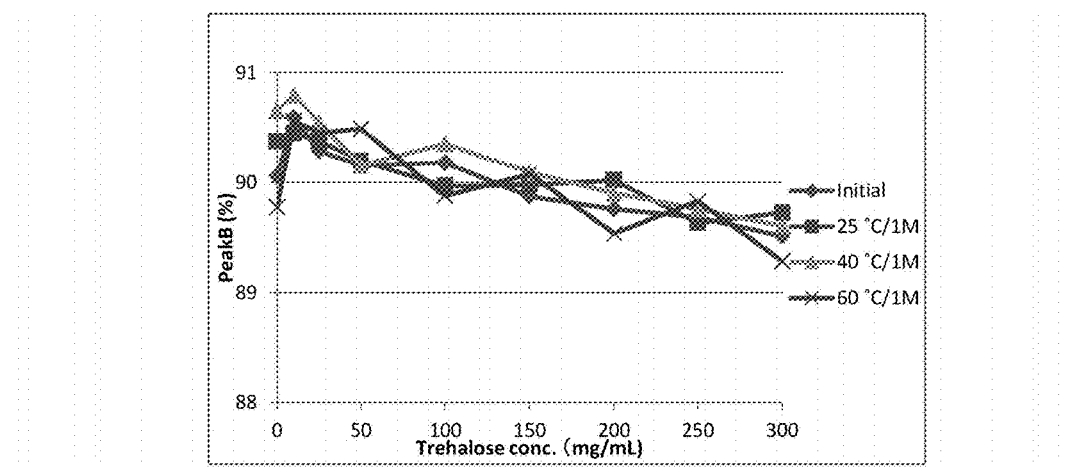
FIG. 6 shows the correlation between the content of trehalose and the ratio of peak B with respect to isoforms in lyophilized formulations tested in Test Example 4.

According to FIG. 6, it was found that the isoform ratio of peak B was decreased with an increase in the content of trehalose in formulations. Similarly, a decrease in the isoform ratio of peak B was also observed for the formulation of Comparative Example 7 which did not comprise trehalose.

Figure 7:
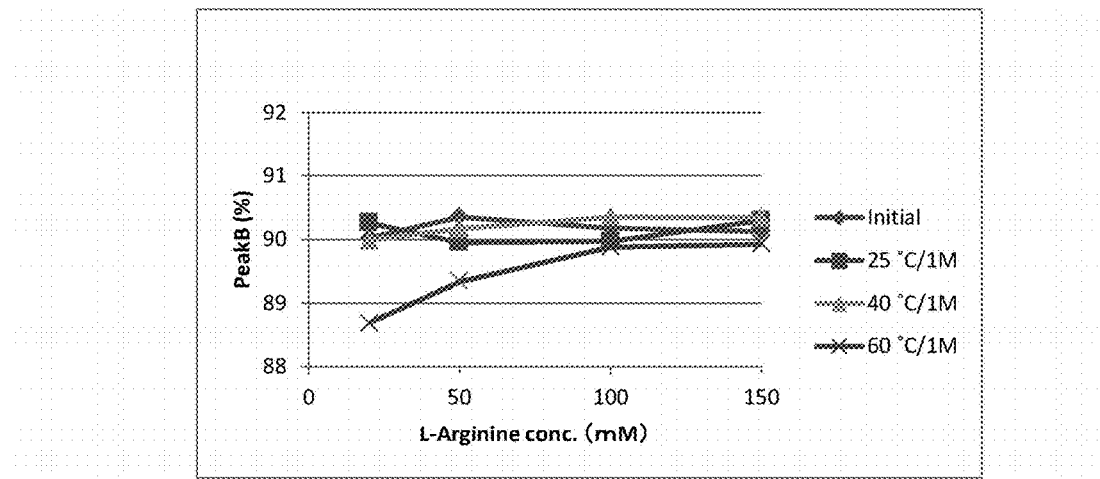
FIG. 7 shows the correlation between the content of arginine and the ratio of peak B with respect to isoforms in lyophilized formulations tested in Test Example 4.

According to FIG. 7, it was found that the isoform ratio of peak B was decreased with a decrease in the content of arginine in formulations under the storage condition of 60° C. for 1 month.

Meanwhile no change in the isoform ratio according to the change in the content of hepatic growth factor in formulations was observed.

TABLE 13

| | Ratio of peak B (%) | | | | | |
|---|---|---|---|---|---|---|
| | | 2-week storage | | | 1-month storage | |
| | Initial | 25° C. storage | 40° C. storage | 60° C. storage | 25° C. storage | 40° C. storage | 60° C. storage |
| Example 1 | 90.59 | 90.10 | 90.89 | 89.81 | 90.87 | 90.87 | 90.68 |
| Example 2 | 90.62 | 90.60 | 90.89 | 90.24 | 90.96 | 90.96 | 90.51 |
| Example 3 | 91.51 | 90.22 | 90.79 | 91.09 | 91.04 | 91.21 | 90.70 |
| Example 4 | 90.69 | 90.84 | 90.58 | 90.59 | 91.08 | 91.05 | 90.70 |
| Comparative Example 1 | 90.28 | 90.74 | 89.79 | 85.37 | 89.94 | 90.06 | 100.00 |
| Comparative Example 2 | 90.82 | 90.89 | 90.62 | 90.07 | 90.71 | 90.78 | 88.93 |
| Comparative Example 3 | 90.53 | 90.99 | 90.84 | 88.44 | 90.75 | 90.52 | 84.56 |
| Comparative. Example 4 | 90.75 | 91.43 | 90.57 | 89.80 | 90.38 | 90.89 | 86.08 |
| Comparative Example 5 | 91.22 | 90.72 | 90.40 | 90.37 | 90.27 | 90.86 | 90.35 |
| Comparative Example 6 | 91.17 | 90.40 | 90.54 | 90.24 | 90.66 | 91.45 | 83.05 |

TABLE 14

| | Ratio of peak B (%) | |
|---|---|---|
| | Initial | 60° C./2-week storage |
| Example 5 | 89.95 | 89.76 |
| Example 6 | 89.89 | 89.89 |
| Example 7 | 89.57 | 89.82 |
| Example 8 | 90.00 | 89.35 |
| Example 9 | 90.23 | 89.73 |
| Example 10 | 89.70 | 89.96 |
| Example 11 | 90.04 | 90.12 |

TABLE 15

| | Ratio of peak B (%) | | | |
|---|---|---|---|---|
| | | 1-month storage | | |
| | Initial | 25° C. storage | 40° C. storage | 60° C. storage |
| Example 12 | 90.09 | 89.94 | 90.38 | 89.66 |
| Example 13 | 90.18 | 89.97 | 90.35 | 89.88 |
| Example 14 | 89.71 | 90.20 | 90.26 | 89.76 |
| Example 15 | 89.71 | 90.00 | 90.20 | 89.86 |
| Example 16 | 90.59 | 90.44 | 90.79 | 90.55 |
| Example 17 | 90.28 | 90.38 | 90.54 | 90.45 |
| Example 18 | 90.15 | 90.19 | 90.15 | 90.49 |
| Example 19 | 89.87 | 89.97 | 90.09 | 90.07 |
| Example 20 | 89.76 | 90.02 | 89.90 | 89.54 |
| Example 21 | 89.68 | 89.63 | 89.76 | 89.83 |
| Example 22 | 89.51 | 89.72 | 89.61 | 89.29 |
| Example 23 | 90.02 | 90.26 | 89.98 | 88.68 |
| Example 24 | 90.35 | 89.95 | 90.17 | 89.34 |
| Example 25 | 90.12 | 90.30 | 90.34 | 89.93 |
| Comparative Example 7 | 90.05 | 90.37 | 90.65 | 89.77 |

Test Example 5

The amount of insoluble aggregates in Examples 1 to 25 and Comparative Examples 1 to 7 was evaluated as follows.

<Method>

Water for injection (1 mL) was added to each lyophilized formulation which was left to stand and then diluted in water for injection or each placebo aqueous solution to give a sample. Each sample was measured on a flow particle imaging analyzer for the number of insoluble microparticles before and after storage and the number of insoluble microparticles was calculated according to the following formula:

$$\text{Number of microparticles (number/vial)} = P \times 1000 \times V/(n \times v)$$

wherein:
P: number of particles detected;
V: volume of the sample solution (mL);
n: number of measurements; and
v: volume of the sample per measurement.

<Results>

The results of measurement of the amount of insoluble aggregates in samples of Examples 1 to 11 and Comparative Examples 1 to 6 initially (before storage) and after storage at 60° C. for 2 weeks or 1 month are shown in Tables 16 and 17.

According to Table 16, the amount of insoluble aggregates in Comparative Examples 1 to 6 was increased after storage at 60° C. for 1 month. According to Tables 16 and 17 meanwhile, such a significant change in the amount of insoluble aggregates as in Comparative Examples was not observed for Examples 1 to 11. Thus generation of insoluble aggregates was suppressed in Examples 1 to 11 even under the storage condition of 60° C. for 1 month. No significant change in the amount of insoluble aggregates was observed for Examples 12 to 25.

TABLE 16

| | Number of insoluble microparticles (number/vial) | | | | | |
|---|---|---|---|---|---|---|
| | <10 μm | | ≥10 μm | | ≥25 μm | |
| | Initial | 60° C./ 1-month storage | Initial | 60° C./ 1-month storage | Initial | 60° C./ 1-month storage |
| Negative control | 6786 | — | 143 | — | 0 | — |
| Example 1 | 13929 | 9286 | 333 | 190 | 0 | 0 |
| Example 2 | 7857 | 3929 | 143 | 95 | 0 | 48 |
| Example 3 | 7143 | 12143 | 286 | 333 | 95 | 48 |
| Example 4 | 19643 | 6429 | 381 | 0 | 95 | 0 |
| Comparative Example 1 | 18571 | 390000 | 333 | 87524 | 190 | 49857 |
| Comparative Example 2 | 15357 | 7857 | 286 | 1095 | 48 | 333 |
| Comparative Example 3 | 30000 | 7392857 | 381 | 1476 | 0 | 48 |
| Comparative Example 4 | 28929 | 334643 | 238 | 70286 | 0 | 24476 |
| Comparative Example 5 | 11071 | 66786 | 143 | 143 | 48 | 0 |
| Comparative Example 6 | 3214 | 5153214 | 238 | 197238 | 48 | 18524 |

TABLE 17

| | Number of insoluble microparticles (number/vial) | | | | | |
|---|---|---|---|---|---|---|
| | <10 μm | | ≥10 μm | | ≥25 μm | |
| | Initial | 60° C./ 2-week storage | Initial | 60° C./ 2-week storage | Initial | 60° C./ 2-week storage |
| Example 5 | 714 | 357 | 0 | 0 | 0 | 0 |
| Example 6 | 714 | 357 | 48 | 48 | 0 | 0 |
| Example 7 | 2143 | 0 | 95 | 0 | 48 | 0 |
| Example 8 | 1071 | 357 | 0 | 0 | 0 | 0 |
| Example 9 | 714 | 1786 | 95 | 48 | 95 | 0 |
| Example 10 | 1429 | 357 | 0 | 190 | 0 | 48 |
| Example 11 | 357 | 357 | 48 | 0 | 0 | 0 |

Test Example 6

Biological activity of Example 1, Comparative Example 5 and Comparative Example 6 was evaluated as follows.

<Method>
Mink lung epithelial cells (Mv.1.Lu cells) were cultured, the viability of cells were confirmed, and a cell solution was then prepared at $1 \times 10^5$/mL. A solution of transforming growth factor β-1 (TGFβ-1) was added to each well of a 96-well assay plate and a sample solution was added to each well at a hepatic growth factor concentration of 0.125, 0.25, 0.5, 1, 2, 4, 8, 16, 32, 64 or 128 ng/mL. The cell solution of $1 \times 10^5$/mL was then added and the plate was incubated in a 5% carbon dioxide incubator at 37° C. for 69 hours. The Cell Counting Kit (10 μL) available from Dojindo Molecular Technologies, Inc. was added to the plate which was then incubated for 3 hours and measured for the absorbance at 450 nm.

The obtained absorbance was plotted on the vertical axis relative to the HGF concentration in the samples (horizontal axis) and EC50 of the samples was calculated using an analytical software (SoftMax Pro available from Molecular Devices) employing parallel line analysis and 4 parameter logistic analysis. The relative titer (%) was calculated by dividing EC50 before storage by EC50 after storage.

<Results>
The relative titer of EC50 of samples of Example 1 and Comparative Examples 5 and 6 after storage at 60° C. for 1 month is shown in Table 18.

According to Table 18, a decrease in the relative titer was observed for Comparative Examples 5 and 6 after storage at 60° C. for 1 month.

Meanwhile no decrease in the relative titer was observed for Example 1, indicating that the biological activity was retained even under the storage condition of 60° C. for 1 month.

TABLE 18

| | Example 1 | Comp. Example 5 | Comp. Example 6 |
|---|---|---|---|
| Relative titer (%) | 101 | 80 | 45 |

INDUSTRIAL APPLICABILITY

The lyophilized formulation of the present invention has an industrial applicability in that it can provide to medical practice hepatic growth factor formulations having high quality.

SEQUENCE LISTING FREE TEXT

SEQ ID NO: 1 represents an amino acid sequence of human hepatic growth factor.

We claim:

1. A lyophilized formulation comprising:

(1) hepatic growth factor (HGF);

(2) trehalose; and (3) one or more compounds comprising arginine, histidine, lysine, meglumine, glutamic acid, aspartic acid, proline, creatine, creatinine, tris(hydroxymethyl)aminomethane, or a pharmaceutically acceptable salt thereof, wherein the mass ratio of HGF to trehalose is from 1:4 to 1:460 and the mass ratio of HGF to each of the one or more compounds is from 1:1 to 1:50 in the lyophilized formulation, and wherein the lyophilized formulation exhibits less than 1.4% of soluble aggregates when it is dissolved in an aqueous solution to 1 mg/mL HGF and evaluated by size exclusion chromatography after being stored at 60° C. for 1 month.

2. A method for stabilizing hepatic growth factor (HGF), the method comprising lyophilizing an aqueous solution to form a lyophilized formulation comprising:

(1) HGF;

(2) trehalose; and (3) one or more compounds comprising arginine, histidine, lysine, meglumine, glutamic acid, aspartic acid, proline, creatine, creatinine, tris(hydroxymethyl)aminomethane, or a pharmaceutically acceptable salt thereof, wherein the mass ratio of HGF to trehalose is from 1:4 to 1:460 and the mass ratio of HGF to each of the one or more compounds is from 1:1 to 1:50 in the lyophilized formulation, and wherein the lyophilized formulation exhibits less than 1.4% of soluble aggregates when it is dissolved in an aqueous solution to 1 mg/mL HGF and evaluated by size exclusion chromatography after being stored at 60° C. for 1 month.

3. A method for producing a lyophilized formulation comprising:

(1) adjusting the pH of an aqueous solution comprising one or more compounds comprising arginine, histidine, lysine, meglumine, glutamic acid, aspartic acid, proline, creatine, creatinine, tris(hydroxymethyl)aminomethane, or a pharmaceutically acceptable salt thereof, to a pH 4.5 to 6.5;

(2) adding hepatic growth factor (HGF) to the aqueous solution after the pH adjustment of step (1)and adding, trehalose to the aqueous solution either before or after the pH adjustment of step (1); and (3) lyophilizing the aqueous solution produced by step (2), wherein the mass ratio of HGF to trehalose is from 1:4 to 1:460 and the mass ratio of HGF to each of the one or more compounds is from 1:1 to 1:50 in the lyophilized formulation, and wherein the lyophilized formulation exhibits less than 1.4% of soluble aggregates when it is dissolved in an aqueous solution to 1 mg/mL HGF and evaluated by size exclusion chromatography after being stored at 60° C. for 1 month.

4. The method of claim 3, wherein trehalose is added to the aqueous solution after the pH adjustment of step (1), simultaneously or sequentially with adding HGF in step (2).

\* \* \* \* \*

UNITED STATES PATENT AND TRADEMARK OFFICE
CERTIFICATE OF CORRECTION

| | |
|---|---|
| PATENT NO. | : 11,547,743 B2 |
| APPLICATION NO. | : 15/305049 |
| DATED | : January 10, 2023 |
| INVENTOR(S) | : Ryo Ohori and Kanta Horie |

It is certified that error appears in the above-identified patent and that said Letters Patent is hereby corrected as shown below:

On the Title Page

Item (56) In U.S. Patent Documents:
Column 2, Line 3, delete "2019/0000623" and insert -- 2019/0062390 --.

In the Claims

Column 27, Line 2, in Claim 3, delete "(1)and adding," and insert -- (1) and adding --.

Signed and Sealed this
Twenty-eighth Day of February, 2023

Katherine Kelly Vidal
*Director of the United States Patent and Trademark Office*